United States Patent
Hohlbaum et al.

(10) Patent No.: US 9,950,034 B2
(45) Date of Patent: *Apr. 24, 2018

(54) METHODS FOR PREVENTING OR TREATING DISORDERS BY INCREASING BIOAVAILABILITY OF IRON AND RELATED PHARMACEUTICAL FORMULATION

(71) Applicant: Pieris Pharmaceuticals GmbH, Freising (DE)

(72) Inventors: Andreas Hohlbaum, Paunzhausen (DE); Hendrik Gille, Munich (DE); Stefan Trentmann, Allershausen (DE); Laurent Audoly, Mahwah, NJ (US); Andrea Allersdorfer, Geisenhausen (DE)

(73) Assignee: PIERIS PHARMACEUTICALS GMBH, Freising (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,146

(22) Filed: Feb. 16, 2017

(65) Prior Publication Data

US 2017/0224770 A1    Aug. 10, 2017

Related U.S. Application Data

(63) Continuation of application No. 14/364,465, filed as application No. PCT/EP2012/075135 on Dec. 12, 2012, now Pat. No. 9,610,356.

(60) Provisional application No. 61/569,501, filed on Dec. 12, 2011, provisional application No. 61/599,152, filed on Feb. 15, 2012.

(51) Int. Cl.
| | |
|---|---|
| *A61K 38/00* | (2006.01) |
| *A61K 38/17* | (2006.01) |
| *A61K 47/48* | (2006.01) |
| *C07K 14/47* | (2006.01) |

(52) U.S. Cl.
CPC .... *A61K 38/1709* (2013.01); *A61K 47/48215* (2013.01); *A61K 47/48415* (2013.01); *C07K 14/47* (2013.01); *C07K 2319/30* (2013.01)

(58) Field of Classification Search
None
See application file for complete search history.

(56) References Cited

U.S. PATENT DOCUMENTS

2010/0160612 A1    6/2010    Skerra et al.

FOREIGN PATENT DOCUMENTS

| WO | WO-2010/033847 A1 | 3/2010 |
| WO | WO-2011/149962 A1 | 12/2011 |
| WO | WO-2012/022742 A1 | 2/2012 |

OTHER PUBLICATIONS

"Pieris Announces Preclinical In Vitro and In Vivo Data for its Anticalin® PRS-080 Hepcidin Antagonist Drug Program," Internet citation, May 23, 2011, XP002661794, retrieved on Oct. 20, 2011.
Holhbaum et al., "Discovery and Preclinical Characterization of a Novel Hepcidin Antagonist with Tunable PK/PD Properties for the Treatment of Anemia in Different Patient Populations," Blood, Nov. 2011, 118(21):314-315, Abstract 687.
International Search Report issued in Application No. PCT/EP2012/075135 dated Jul. 19, 2013.
Siah et al.; "Normal Iron Metabolism and the Pathophysiology of Iron Overload Disorders"; Clin. Biochem Rev. 27:5-16 (Feb. 2006).
Srinivasan et al., "Lipocalin 2 Deficiency Dysregulates Iron Homeostasis and Exacerbates Endotoxin-Induced Sepsis," J. Immunol., Jul. 11, 2012, 189(4):1911-1919.

*Primary Examiner* — Jeanette Lieb
(74) *Attorney, Agent, or Firm* — Foley & Lardner LLP

(57) ABSTRACT

The present disclosure relates to methods of treating, ameliorating or preventing a disorder comprising administering a therapeutically effective amount of a composition to a subject in need thereof, which composition contains a lipocalin mutein or a fragment or a variant thereof capable of increasing the bioavailability of iron in the subject.

20 Claims, 20 Drawing Sheets

Mouse

Rat

| | | mouse | | rat | | cyno | |
|---|---|---|---|---|---|---|---|
| | | $V_D$ [ml] | $C_L$ [ml/h] | $V_D$ [ml] | $C_L$ [ml/h] | $V_D$ [ml] | $C_L$ [ml/h] |
| 1 | SEQ ID NO: 1 + PEG12 | 3.32 | 0.353 | 27.33 | 4.025 | 300.89 | 34.09 |
| 2 | SEQ ID NO: 1 + PEG20 | 3.58 | 0.161 | 19.05 | 1.253 | 488.67 | 19.73 |
| 3 | SEQ ID NO: 1 + PEG30 | 1.88 | 0.067 | 15.47 | 0.572 | 239.0 | 4.5 |
| 4 | SEQ ID NO: 1 + PEG40 | 3.1 | 0.075 | 15.85 | 0.297 | 337.6 | 1.75 |

Figure 2a
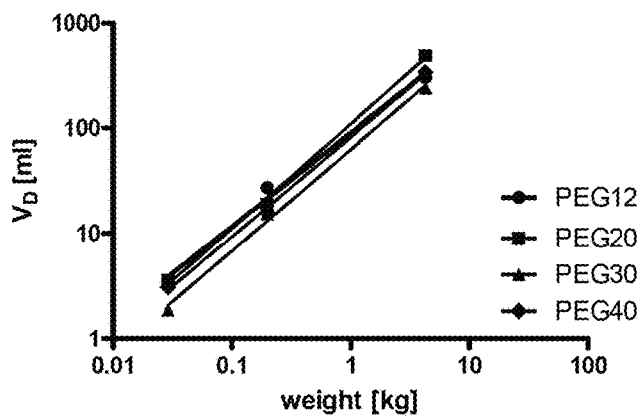
Figure 2b
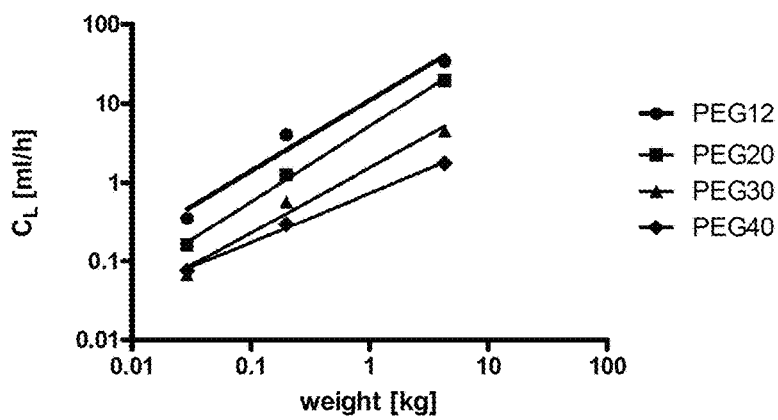
Figure 2c
Goodness of fit ($R^2$)
| | SEQ ID NO: 1 + PEG12 | SEQ ID NO: 1 + PEG20 | SEQ ID NO: 1 + PEG30 | SEQ ID NO: 1 + PEG40 |
|---|---|---|---|---|
| $V_D$ | 0.99 | 0.99 | 0.99 | 1.0 |
| $C_L$ | 0.98 | 1.0 | 0.98 | 0.99 |

Figure 2d

Extrapolated values for human $V_D$ and $C_L$ and calculated values for $K_{el}$ and $t_{1/2}\beta$

|  | $V_D$ (ml) | $C_L$ (ml/h) | $K_{el}$ (1/h) | $t_{1/2}\beta$ (h) |
|---|---|---|---|---|
| SEQ ID NO: 1 + PEG12 | 5093.3 | 633.8 | 0.124 | 5.6 |
| SEQ ID NO: 1 + PEG20 | 9572 | 389.9 | 0.041 | 17 |
| SEQ ID NO: 1 + PEG30 | 3723.9 | 51.4 | 0.0138 | 50 |
| SEQ ID NO: 1 + PEG40 | 4497.8 | 10.5 | 0.0023 | 298 |

Figure 3

| Antagonist | IC50 [pM] | STDV [pM] | mean of n=X |
|---|---|---|---|
| SEQ ID NO: 2 | 56 | 23 | 6 |
| SEQ ID NO: 1 linked to PEG12 | 48 | 14 | 5 |
| SEQ ID NO: 1 linked to PEG20 | 47 | 11 | 5 |
| SEQ ID NO: 1 linked to PEG30 | 58 | 6 | 6 |
| SEQ ID NO: 1 linked to PEG40 | 54 | 10 | 5 |

Figure 4

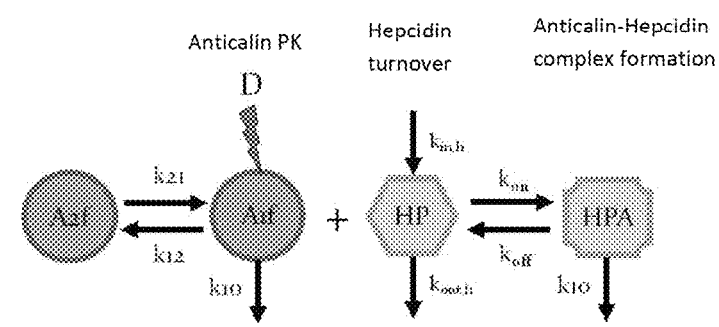

Free anticalin $\quad \dfrac{dA1f}{dt} = -k_{10} \cdot A1f - k_{12} \cdot A1f + k_{21} \cdot A2f - k_{on} \cdot HP \cdot \dfrac{A1f}{Vc} + k_{off} \cdot HPA$ Free hepcidin $\quad \dfrac{dHP}{dt} = k_{in,h} - k_{out,h} \cdot HP - k_{on} \cdot HP \cdot \dfrac{A1f}{Vc} + k_{off} \cdot HPA$ Complex $\quad \dfrac{dHPA}{dt} = k_{on} \cdot HP \cdot \dfrac{A1f}{Vc} - k_{off} \cdot HPA - k_{10} \cdot HPA$ Total anticalin (measured) $\quad C_{tot} = \dfrac{A1f + HPA}{Vc}$

Figure 13a

| Binder | Analyte | ka [M⁻¹*s⁻¹] | kd [s-1] | Kd [nM] | N |
|---|---|---|---|---|---|
| SEQ ID NO: 1 | Hepcidin-25 | 3,8 (± 1,5) • $10^6$ | 2,0 (± 0,7) • $10^{-4}$ | 0,07 (± 0,05) | 6 |
| SEQ ID NO: 1 | Fe-enterobactin | No binding | | | 8 |
| SEQ ID NO: 1 | β-defensin | No binding | | | 3 |
| SEQ ID NO: 1 | VEGF8-109 | No binding | | | 3 |
| SEQ ID NO: 1 | HSA | No binding | | | 3 |
| SEQ ID NO: 4 | Hepcidin-25 | No binding | | | 6 |
| SEQ ID NO: 4 | Fe-enterobactin | 2,1 (± 0,7) • $10^6$ | 8,3 (± 1,1) • $10^{-4}$ | 0,42 (± 0,14) | 3 |

Figure 13b

| Binder | Analyte | Kd [nM] | N |
|---|---|---|---|
| SEQ ID NO: 1 | Hepcidin-25 | 0.10(±0.07) | 3 |
| SEQ ID NO: 1 | cynomolgus hepcidin 25 | 0.07(±0.06) | 3 |

METHODS FOR PREVENTING OR TREATING DISORDERS BY INCREASING BIOAVAILABILITY OF IRON AND RELATED PHARMACEUTICAL FORMULATION

CROSS-REFERENCE TO RELATED APPLICATIONS

This application is a Continuation of U.S. application Ser. No. 14/364,465, filed Jun. 11, 2014, now U.S. Pat. No. 9,610,356, which is the U.S. National Stage of PCT Application No. PCT/EP2012/075135, filed Dec. 12, 2012, which claims priority from Provisional U.S. Application 61/569,501, filed Dec. 12, 2011, and from Provisional U.S. Application 61/599,152, filed Feb. 15, 2012, all of which are incorporated herein by reference in their entirety.

FIELD OF THE INVENTION

The present disclosure relates to methods of treating, ameliorating or preventing a disorder comprising administering a therapeutically effective amount of a composition to a subject in need thereof, which composition contains a lipocalin mutein or a fragment or a variant thereof capable of increasing the bioavailability of iron in the subject. The bioavailability of iron may be increased, for example, in a body fluid such as blood. The disorder is preferably associated with an altered level of iron in the subject. In further embodiments, the disease or disorder involves a disorder of iron homeostasis or an inflammatory condition associated with, for instance, a decreased level of iron in a body fluid such as blood. The present disclosure also relates to a concentrated, stable pharmaceutical formulation of at least one lipocalin mutein capable of increasing the bioavailability of iron in a body fluid such as blood of a subject in need thereof. The concentrated formulation can, for example, be suitable for subcutaneous administration via a number of conventional delivery devices such as a syringe. Further, a composition containing a lipocalin mutein can include any of a wide range of half-life extending moieties (including protein or non-protein based moieties), yielding different compositions having different half-lives (pharmacokinetic profile) in a subject.

BACKGROUND

Proteins that selectively bind to selected targets by way of non-covalent interaction play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used.

Additional proteinaceous binding molecules that have antibody-like functions are the members of the lipocalin family, which have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homoeostasis (reviewed, for example, in Flower, D. R. (1996) *Biochem. J.* 318, 1-14 and Flower, D. R. et al. (2000) *Biochim. Biophys. Acta* 1482, 9-24).

Lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350).

Various PCT publications (e.g., WO 99/16873, WO 00/75308, WO 03/029463, WO 03/029471 and WO 2005/19256) disclose how muteins of various lipocalins (e.g. NGAL lipocalin) can be constructed to exhibit a high affinity and specificity against a target that is different than a natural ligand of a wild type lipocalin. This can be done, for example, by mutating one or more amino acid positions of at least one of the four peptide loops. In addition, PCT publication WO 2012/022742 teaches methods for generation of lipocalin muteins directed against hepcidin.

Hepcidin, a peptide hormone typically existing in two forms made of either 20 or 25 amino acids, produced predominantly in hepatocytes of the liver, plays a central role in the regulation of iron homeostasis, acts as an antimicrobial peptide and is directly or indirectly involved in the development of most iron-deficiency/overload syndromes. A major action of hepcidin is to internalize and degrade the iron exporter ferroportin, which is expressed on all iron-exporting cells. Hepcidin directly binds to ferroportin. A low concentration of hepcidin level leads to acceleration of iron release from macrophages and hepatocytes.

Methods of isolating, analyzing and quantifying hepcidin as well as agents for the treatment of diseases and/or conditions associated with decreased levels of iron have been described in international patent applications WO 2008/011158, WO 2008/097461, WO 2009/094551A1, WO 2009/139822, WO 2009/058797 and WO 2010/017070. However, no no protein having the features attendant to the proteins provided by present disclosure has been previously described.

Therefore, it would be desirable to have improved therapeutic methods involving therapeutically effective amount of a composition comprising at least one mutein of human NGAL lipocalin, which is capable of increasing the bioavailability of iron in a body fluid such as blood and exhibits in vivo therapeutic activities in a subject in need thereof.

BRIEF DESCRIPTION OF THE FIGURES

FIGS. 2a-2d show allometric scaling of the volume of distribution, $V_D$ and clearance, $C_L$ values obtained in the single dose PK studies with PEGylated versions of a lipocalin mutein in mice, rat and cyno (FIG. 2a and FIG. 2b), the goodness of fit ($R^2$) for the linear regression analysis (FIG. 2c) and scaled values for human volume of distribution, $V_D$ and clearance, $C_L$ of the PEGylated lipocalin muteins (FIG. 2d). In addition, elimination rate constant and human half-life were calculated from the estimated human values for $V_D$ and $C_L$ as $k_{el}=C_L/V_D$ and $t_{1/2}=\ln 2/k_{el}$.

FIG. 3 shows solution competition ELISA based inhibition of biotinylated hepcidin binding to a hepcidin specific monoclonal antibody (antibody 12B9 disclosed in WO 2008/097461, the variable light and heavy chain regions are shown in SEQ ID NOs: 6 and 7, respectively). The assay measures free/non-bound hepcidin and is highly sensitive, as a very low concentration of Hepcidin-25 (25 pM) is used in the assay. Four PEG conjugates of a lipocalin mutein bind Hepcidin-25 in solution with picomolar affinity IC50 values, which are not affected by different half-life extension formats.

FIG. 4 shows the Pharmacokinetic and pharmacodynamic (PK/PD) model structure developed for the interaction between hepcidin and PEG conjugates of a lipocalin mutein. A1f and A1f refer to the amount of free conjugate derivative in the central and peripheral compartment of the pharmacokinetic model. HP is the amount of free hepcidin in the systemic circulation, HPA the conjugate-hepcidin complex. K21, k12 and k10 or first-order rate constants, kin,h and kout,h are turnover rate constants for hepcidin. kon and koff are binding constants for the formation and dissociation of the conjugate-hepcidin complex. Vc is the volume of distribution of the central compartment for the conjugates. D denotes the dose.

FIGS. 13a-13b show an analysis of the affinity and specificity of a lipocalin mutein having the sequence of SEQ ID NO: 1 using Biacore. In particular, the FIGS. 13a-13b show kinetic parameters and binding affinity of a lipocalin mutein to Hepcidin-25 and other related and unrelated molecules.

DETAILED DESCRIPTION

Figure 1A:
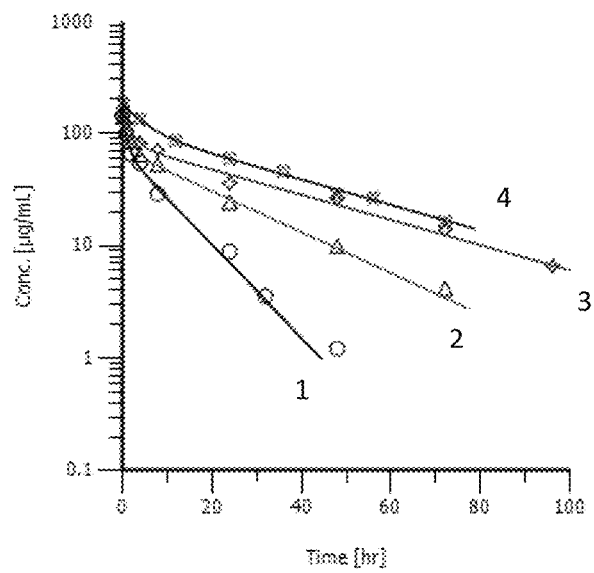
FIGS. 1a-1d show plasma concentration profiles of PEGylated versions of a lipocalin mutein, single dose intravenous (i.v.), at 10 mg/kg, two-compartmental pharmacokinetic (PK) analysis in mice (FIG. 1a), rat (FIG. 1b), cyno (FIG. 1c) and key pharmacokinetic parameters such as volume of distribution, $V_D$ and clearance, $C_L$ (FIG. 1d). The data shows that PK properties of a lipocalin mutein can be tuned e.g. through the choice of PEG. In addition, allometric scaling of PK data from mice, rats and non-human primates allows the prediction of human PK properties such as half-life.

The present disclosure relates to a method of treating, ameliorating or preventing a disorder comprising administering to a subject in need thereof, preferably, a therapeutically effective amount of a lipocalin mutein or fragments or variants thereof that is capable of increasing the bioavailability of iron in the subject, said lipocalin mutein or fragments or variants thereof are preferably in the form of a pharmaceutical composition. Likewise, the present disclosure relates to a lipocalin mutein or fragments or variants thereof that is capable of increasing the bioavailability of iron in a subject for use in a method of treating, ameliorating or preventing a disorder comprising administering to a subject in need thereof. In some preferred embodiments, the composition is administered to a subject in need thereof at a frequency, for example, selected from the group consisting of: up to twice daily, up to once daily, up to once every other day, up to once every third day, up to twice every week, up to once every week and up to once every other week and up to once every month.

The disorder that is preferably treated, ameliorated or prevented is associated with an altered level of iron in the subject in need thereof.

In related embodiments, the disease or disorder involves a disorder of iron homeostasis or an inflammatory condition associated with a decreased level of iron in, for example, a body fluid such as blood.

In various preferred embodiments, the disorder is anemia of inflammation or iron-deficiency anemia, preferably the anemia of inflammation is associated with anemia of chronic diseases (ACDs) or anemia of chronic disorders.

A pharmaceutical composition provided for herein contains a lipocalin mutein that is capable of increasing the bioavailability of iron in the subject. In some embodiments, a lipocalin mutein described herein that is capable of increasing the bioavailability of iron in the subject is a lipocalin mutein that is capable of inhibiting binding of hepcidin to a hepcidin specific monoclonal antibody (antibody 12B9 disclosed WO 2008/097461, the variable light and heavy chain regions are shown in SEQ ID NOs: 6 and 7, respectively, while in WO 2008/097461 the variable light and heavy chain regions of the 12B9 are shown in SEQ ID NOs: 158 and 160). It is thus assumed that the lipocalin mutein binds to/recognizes the same epitope as said monoclonal antibody. Hence, the present invention also provides a lipocalin mutein that competes for binding to hepcidin with the 1269 antibody having the variable light and heavy chain regions shown in SEQ ID NOs: 6 and 7, respectively. Such lipocalin muteins are preferably applied in the methods and uses as described herein. In some embodiments, a lipocalin mutein described herein that is capable of increasing the bioavailability of iron in the subject may be a human NGAL lipocalin (also "hNGAL") mutein which has at any two or more amino acids at a position corresponding to position 96, 100, and/or 106 of the linear polypeptide sequence of the mature human tear lipocalin a mutated amino acid. The lipocalin mutein further may have at any one or more amino acids at a position corresponding to position 36, 40, 41, 49, 52, 68, 70, 72, 73, 77, 79, 81, 96, 100, 103, 106, 125, 127, 132, and/or 134 of the linear polypeptide sequence of hNGAL a mutated amino acid. The lipocalin mutein described herein may have in a particularly preferred embodiment at least 75% identity to the sequence of mature human NGAL lipocalin.

In some further embodiments, the lipocalin mutein that is capable of increasing the bioavailability of iron in the subject is a lipocalin mutein that is represented by SEQ ID NO: 1 or a fragment or variant thereof. Preferably, the fragment or variant has a sequence identity or homology of at least a 75%, 80%, 85%, 90% or 95% to the amino acid represented by SEQ ID NO: 1. In this regard, the SEQ ID NOs: 1-14 as disclosed in WO 2012/022742 are hereby incorporated by reference in their entirety. These lipocalin muteins can therefore be applied in the methods and uses described herein.

In various preferred embodiments, it is possible to attach a half-life altering moiety to a lipocalin mutein of the disclosure, to alter the half-life and, therefore, pharmacokinetic profile, of the lipocalin mutein. One way to do this is to mutate or add at least one amino acid residue in the lipocalin mutein that is capable of serving as a point of attachment for the half-life altering moiety. This can be, for example, the addition of (or substitution to) cysteine to introduce a reactive group, for example, for the conjugation to other compounds, such as polyethylene glycol (PEG), hydroxyethyl starch (HES), biotin, peptides or proteins, or for the formation of non-naturally occurring disulphide linkages. With respect to a mutein of human NGAL, exemplary possibilities of such a mutation to introduce a cysteine residue into the amino acid sequence of a hNGAL mutein to include the introduction of a cysteine (Cys) residue at least at one of the sequence positions that correspond to sequence positions 14, 21, 60, 84, 88, 116, 141, 145, 143, 146 or 158 of the wild type sequence of hNGAL. In some embodiments where a hNGAL mutein has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate a hNGAL mutein, for example, in order to increase the serum half-life of a respective hNGAL mutein.

In this regard, a lipocalin mutein provided for herein may be modified to alter its pharmacokinetic properties in a subject. For example, the terminal half-life of a lipocalin mutein may contain a PEG moiety ranging from 5 kilo Dalton to 40 kilo Dalton or even greater. The half-life of a pharmaceutical composition disclosed herein (as modified to increase its half-life) preferably is at least about one, two, four, six, seven, fourteen or twenty one days in the subject. With studies as performed in the Examples, the skilled can triangulate the influence of the PEG length on: (i) PK properties in animals and humans, and (ii) Pharmacodynamic (PD) responses (e.g. how long a lipocalin mutein is able to inhibit hepcidin or to increase serum iron at a given dose and hepcidin turn over rate). As shown from the data of said studies, a certain half-life is required to maintain sufficiently high concentration of the lipocalin mutein in the body of a subject, so the lipocalin mutein will have a chance to bind hepcidin before the lipocalin mutein is cleared.

In various preferred embodiments, PEG30 or PEG40 would be suggested in animals/humans with normal renal filtration rather than shorter PEGs because i.e. the faster elimination of PEG12 or PEG20 limits their effectiveness and duration of hepcidin neutralisation. As shown in Example 7 and FIG. 8, the PEG12 conjugate resulted in lower peak serum iron levels and shorter duration of elevated serum iron levels above baseline.

Figure 7A:
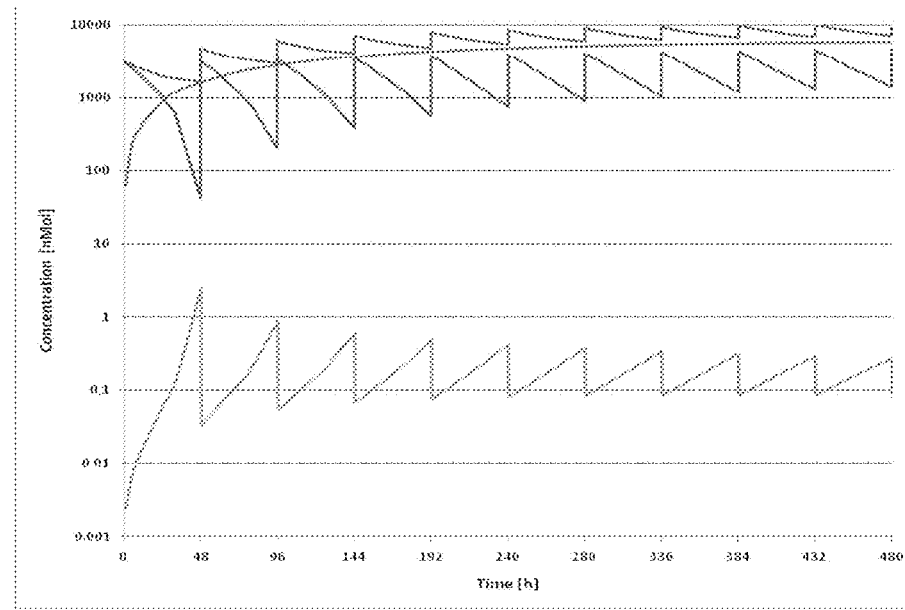
FIGS. 7a-7b show the simulated concentration-time profiles (nMol) of total (bound and unbound) lipocalin mutein (red), hepcidin-mutein complex (blue), free lipocalin mutein (green) and free hepcidin (red) after repeat administration of 10 mg/kg of a PEGylated lipocalin mutein to Cynomolgus monkeys. The FIGS. 7a-7b also show simulated concentration-time profiles (nMol) of total (bound and unbound) conjugate (red), hepcidin-conjugate complex (blue), free conjugate (green) and free hepcidin (red) after repeat administration of 10 mg/kg of two PEG conjugates of a lipocalin mutein every 48 hours to Cynomolgus monkeys.
Figure 7B:
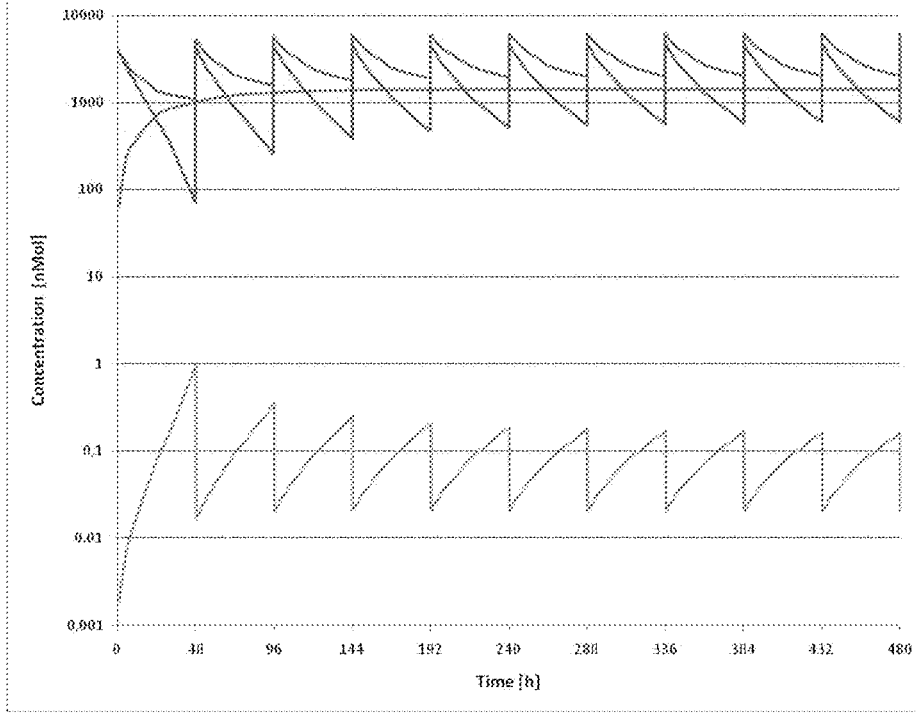

In addition, as shown in Example 6 and FIGS. 7a-7b, binding of hepcidin to the lipocalin mutein contributed to the observed clearance rate of hepcidin-free lipocalin mutein. The speed of this process depends on (i) the hepcidin plasma concentration (nM) in different diseases, and (ii) the underlying production rate in different diseases. In normal animals/humans, the production rate is relative high, so that clearance of the hepcidin-free lipocalin mutein is dominated by hepcidin binding rather than clearance e.g. by renal filtration for the lipocalin mutein, just like the case for other antagonists (such as antibodies) with long serum half-life. Therefore, in a further preferred embodiment, PEG30 would be suggested. On the one hand, a constant suppression of serum hepcidin below a threshold value of 1 nM can be achieved by both the lipocalin mutein-PEG30 conjugate and the lipocalin mutein-PEG40 conjugate, on the other hand, repeat administration of the lipocalin mutein conjugated to PEG40 leads to an approximate 5× higher accumulation of conjugate/hepcidin complexes compared to the lipocalin mutein conjugated to PEG30, without contributing to more efficacy.

Nevertheless, since there are two variables (renal filtration and hepcidin production rate) varying in different diseases, the lipocalin mutein can be optimized for specific patient populations suffering from specific diseases. For example, impaired renal filtration in patients with Chronic Kidney Disease (CKD) or particular cancers might reduce the clearance rate of shorter PEG variants, and in these cases, shorter PEG variants likely have a half-life more comparable to the disclosed PEG30 or PEG40 in normal animals/humans. Thus, in various preferred embodiments, a shorter PEG would be preferred. In addition, the viscosity of a PEGylated lipocalin mutein of the disclosure increases with the PEG size. Because shorter PEG moieties would support formulations with higher concentrations that are still syringeable, for example, for subcutaneous injection, in various particular embodiments, a shorter PEG would be preferred.

In various preferred embodiments, the PK properties such as half-life of a composition containing a lipocalin mutein of the disclosure can also be altered by a protein that, itself, extends the serum half-life of the mutein. The mutein can, for example, be conjugated or expressed as a fusion protein with a moiety selected from the group consisting of an Fc part of an immunoglubolin, a CH3 domain of an immoglobulin, a CH4 domain of an immunoglubulin, an albumin-binding peptide, and an albumin-binding protein.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the disclosure which may be substituted may very due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the disclosure it is preferably to be understood that nucleotides/amino acids may differ in the indicated number but may still have similar neighbouring nucleotides/amino acids. Said nucleotides/amino acids which may be exchanged, deleted or added are also comprised by the term "corresponding position". When used herein "at a position corresponding to a position" a position in a "query" amino acid (or nucleotide) sequence is meant that corresponds to a position in a "subject" amino acid (or nucleotide) sequence.

The term "fragment" as used in the present disclosure in connection with the muteins of the disclosure relates to proteins or peptides derived from full-length mature human tear lipocalin that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature human tear lipocalin and are usually detectable in an immunoassay of mature human tear lipocalin.

The term "variant" as used in the present disclosure relates to derivatives of a protein or peptide that comprise modifications of the amino acid sequence, for example by substitution, deletion, insertion or chemical modification. Preferably, such modifications do not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

The term "human neutrophil gelatinase-associated lipocalin" or "hNGAL" or "lipocalin 2" or "Lcn2" as used herein to refer to the mature human NGAL with the SWISS-PROT/UniProt Data Bank Accession Number P80188 or the mature human NGAL shown in SEQ ID NO: 4. The mature form of this protein has amino acids 21 to 198 of the complete sequence, since a signal peptide of amino acids 1-20 is cleaved off. The protein further has a disulfide bond formed between the amino acid residues at positions 76 and 175 of the mature protein.

Iron metabolism is a set of chemical reactions maintaining the homeostasis of iron. In the human body, iron is present in virtually all cells and is involved in numerous vital functions, for example, it can serves as a carrier of oxygen to the tissues from the lungs in the form of hemoglobin, as a transport medium for electrons within the cells in the form of cytochromes, and/or as an integral part of enzyme reactions in various tissues. Therefore, the regulation of iron is an important part of many aspects of human health. Disturbances of the iron metabolism can lead to different diseases, for instance, anemia.

Hepcidin is the central negative regulator of iron homeostasis. Hepcidin production increases with iron loading and inflammation and decreases under low iron conditions and hypoxia. Hepcidin acts via binding to the only known mammalian cellular iron exporter, ferroportin, and induces its internalization and degradation. Since ferroportin is expressed in the duodenal enterocytes, spleen, and liver, hepcidin increase, and the subsequent decrease of ferroportin, results in the inhibition of duodenal iron absorption, release of recycled iron from macrophages, and mobilization of iron stores in the liver. Hepcidin is thought to play a critical role in the development of anemia associated with inflammatory disease. Acute or chronic inflammatory conditions result in the up-regulation of hepcidin expression, leading to iron deficiency, which can cause anemia associated with inflammatory disease (ACD), cancer (AC, CIA) and Chronic Kidney Disease (CKD) (anemia of CKD).

The term "hepcidin" refers to the protein also termed liver-expressed antimicrobial peptide 1 or putative liver tumor regressor, the human form of which has the UniProtKB/Swiss-Prot accession number P81172. On a general basis, the term "hepcidin" refers to any form of the hepcidin protein known to be present in vertebrate species, including in mammals, but preferably, in primates (e.g. Cynomolgous monkeys or humans). The human unprocessed protein has a length of 84 amino acids and is encoded by the gene "HAMP," also known as "HEPC" or "LEAP1." It is cleaved into two chains, which are herein also included in the term "human hepcidin." These two chains are of amino acids 60-84, which is Hepcidin-25 (Hepc25), and of amino acids 65-84, which is Hepcidin-20 (Hepc20), respectively. Hepcidin-25 is arranged in the form of a bent hairpin, stabilized by four disulfide bonds. Natural variants also included in the term "human hepcidin" have, for example, the amino acid replacement 59 R→G (VAR_0425129); the amino acid replacement 70 C→R (VAR_042513); the amino acid replacement 71 G→D (VAR_026648) or the amino acid replacement 78 C→Y (VAR_042514). A further natural variant is Hepcidin-22, another N-terminally truncated isoform (besides Hecidin-20) of Hepcidin-25.

The term "mature hepcidin" as used herein refers to any mature, bioactive form of the hepcidin protein expressed in a vertebrate such as a mammal. The term "human hepcidin" refers to any form of the hepcidin protein present in humans. The expression "Hepcidin-25" refers to the mature form of human hepcidin with the amino acid sequence as depicted in SEQ ID NO: 5. In some embodiments, one or more lipocalin muteins of the disclosure are able to bind each given form of human hepcidin including proteolytic fragments thereof, regardless of whether the respective hepcidin molecule displays biological/physiological activity. Thus, the hepcidin molecule may only be present in a biological sample, without having any measurable physiological relevance. For example, Hepcidin-22 that so far has only been detected in urine found in urine and that so far is assumed to merely be a urinary degradation product of Hepcidin-25 (reviewed in Kemna et al., Haematologica. 2008 January; 93:(1)90-97). A lipocalin mutein of the disclosure may of course also bind physiological active species such as the mature, bioactive Hepcidin-25. Accordingly, a lipocalin mutein of the disclosure may be used in various pharmaceutical applications, depending on the human hepcidin form chosen to be recognized.

Therefore, a lipocalin mutein according to the disclosure may be used to increase iron levels in a body fluid such as blood, by blocking the interaction with the hepcidin receptor, ferroportin. As a result, internalization and degradation of ferroportin are prevented. The lipocalin mutein thereby supports erythropoiesis by allowing mobilization of stored iron and improved enteral iron absorption. Thus, an illustrative example of a subject in need of an application of the disclosure is a subject hyporesponsive to erythropoiesis stimulating agent (ESA)-therapy (about 40-50% of patients) which is thought to be caused by the decreased availability of iron for the synthesis of hemoglobin due to upregulated hepcidin. A lipocalin mutein according to the disclosure may also be used to increase reticulocyte count, red blood cell count, hemoglobin, and/or hematocrit in a subject, e.g. a human. A pharmaceutical composition comprising a lipocalin mutein of the disclosure may be used in this regard.

Another aspect of the present disclosure relates to a method of treating a subject suffering from a disease or disorder that is associated with a decreased level of iron in a body fluid such as blood, involving administering a lipocalin mutein of the disclosure or a pharmaceutical composition comprising a lipocalin mutein of the disclosure to a subject in need thereof. A respective disease or disorder may include a genetic or a non-genetic disease/disorder causing iron deficiency or overload. A disease state or disorder may include an infectious disease involving e.g. bacteria, fungi, yeast or viruses. As explained above, in some embodiments the disease or disorder is anemia, including, but not limited to, anemia resulting from infection, inflammation, chronic disease, and/or cancer. It may in some embodiments include an inflammatory disease such as arthritis and certain cancer types, a liver disease or a haematological disease. In some embodiments, the disease associated with a decreased level of iron is an aemia or a chronic kidney disease or an anemia associated with chronic kidney disease.

One or more lipocalin muteins of the disclosure may for instance also be used to treat a subject having a decreased level of iron, a disorder of iron homeostasis, anemia or inflammatory condition associated with a decreased level of iron. The subject may, for example, be a mammal such as a human suffering from African iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (in particular anemia associated with chronic kidney disease), including end stage renal disease or chronic renal/kidney failure, cirrhosis of liver, classic hemochromatosis, collagen-induced arthritis (CIA), a condition involving hepcidin excess (elevated hepcidin), congenital dyserythropoietic anemia, congestive heart failure, Crohn's disease, diabetes, a disorder of iron biodistribution, a disorder of iron homeostasis, a disorder of iron metabolism, ferroportin disease, ferroportin mutation hemochromatosis, folate deficiency, Friedrich's ataxia, funicular myelosis, gracile syndrome, a bacterial infection such as *H. pylori* infection, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, a viral infection such as HIV, Huntington's disease, hyperferritinemia, hypochromic microcytic anemia, hypoferremia, insulin resistance, iron deficiency anemia, an iron deficiency disorder, an iron overload disorder, an iron-deficiency condition with hepcidin excess, juvenile hemochromatosis (HFE2), multiple sclerosis, a mutation of a gene involved in iron metabolism, for instance expressing a protein involved therein such as transferrin receptor 2, HFE, hemojuvelin or ferroportin, neonatal hemochromatosis, a neurodegenerative disease related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, a red blood cell disorder, rheumatoid arthritis, sepsis, sideroblastic anemia, systemic lupus erythematosus, thalassemia, thalassemia intermedia, transfusional iron overload, a tumor, vasculitis, vitamin B6 deficiency, vitamin B12 deficiency Wilson's disease, or inflammatory condition associated with a decreased level of iron.

As a further illustrative example, a lipocalin mutein according to the present disclosure can in some embodiments be used in combination with erythropoietin. Anemia in patients with cancer (AC) and/or chronic disease (ACD) are associated with high concentrations of hepcidin (about 30 nmol/L) leading to serum iron deficiency and thus to reduced erythropoiesis. Subjects with baseline hepcidin concentrations below 13 nmol/L in serum have been reported to show a better response to erythropoietin (EPO) therapy than subjects with concentrations above 13 nmol/L. Therefore, treating those patients with a lipocalin mutein capable of increasing the bioavailability of iron in a subject can improve their response to erythropoietin.

The subject in need of an application of the disclosure may be a mammal, such as a human, a dog, a mouse, a rat, a pig, an ape such as Cynomolgous monkeys to name only a few illustrative examples. The term "subject" refers to a vertebrate animal, including a mammal, and in particular a human, in which case the term "patient" can also be used. In some embodiments, the subject may have a disorder that would benefit from an increase in bioactivity of iron in serum, reticulocyte count, red blood cell count, hemoglobin, and/or hematocrit.

The amount of the pharmaceutical composition that can be administered to a subject in methods of the disclosure should be sufficient to yield a satisfactory therapeutic readout in said subject. As used herein, "satisfactory therapeutic readout" can be any one or more of the following: (i) significantly increasing the serum iron level in the subject, (ii) antagonizing hepcidin binding to its receptor and blocking cellular ferroportin (FPN) internalization and degradation in the subject, (iii) significantly enhancing iron restricted erythropoiesis in the subject, (iv) significantly increasing the blood hemoglobin level in the subject, (v) enhancing the responsiveness of the subjects to an ESA and (vi) decreasing the frequency of necessary blood transfusions in the subject.

The quantitative amount of a pharmaceutical composition that can be administered to a subject can, however, span a wide range and frequency. For example, the amount of administered pharmaceutical composition may be as low as 1 mg/kg every four weeks or as high as 40 mg/kg every second day. Preferably, the amount at each dose is selected from the group consisting of: at least 0.1 mg/kg, at least 1 mg/kg, at least 5 mg/kg, at least 10 mg/kg, at least 20 mg/kg, at least 40 mg/kg in the subject, while the frequency of administration may be not less frequent than a period of time selected from the group consisting of: every four weeks, every two weeks, every week, twice per week, every second day or daily.

The disclosure also relates to in the disclosed methods using a pharmaceutical composition that includes at least one lipocalin mutein of the disclosure or a fusion protein or conjugates thereof and, optionally, a pharmaceutically acceptable excipient.

In the disclosed methods, the pharmaceutical composition may be administered/dosed to a subject in a variety of methods, including via any parenteral or non-parenteral (enteral) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures. Where administration is via intravenous infusion, the pharmaceutical composition can be administered over a period of time selected from the group consisting of: up to fifteen minutes, up to thirty minutes, up to one hour, up to two hours and up to three hours.

Accordingly, one or more lipocalin muteins of the present disclosure can be formulated into compositions using pharmaceutically acceptable ingredients as well as established methods of preparation (Gennaro and Gennaro (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used.

In various preferred embodiments, the formulation contains said one or more lipocalin muteins may be a highly concentrated, stable pharmaceutical formulation that comprises: about 50 to 350 mg/ml the lipocalin mutein; about 1 to 100 mM of a buffering agent providing a pH of 5.5 to 8; about 1 to 500 mM of a stabilizer or a mixture of two or more stabilizers (e.g. $NaCl_2$, sucrose, sorbitol or methionine); about 0.01 to 0.08% of a non-ionic surfactant; and an effective amount of at least one hyaluronidase enzyme.

Several references and documents are cited throughout the text of this specification. Each of the documents cited herein (including all patents, patent applications, scientific publications, SWISS-PROT Data Bank Accession Numbers, Swiss-Prot IDs, UniProt IDs, etc.), whether supra or infra, are hereby incorporated by reference in their entirety. Nothing herein is to be construed as an admission that the disclosure is not entitled to antedate such disclosure by virtue of prior disclosure.

The following non-limiting Examples and Figures further illustrate various aspects of the present disclosure.

EXAMPLES

Example 1

Figure 1B:
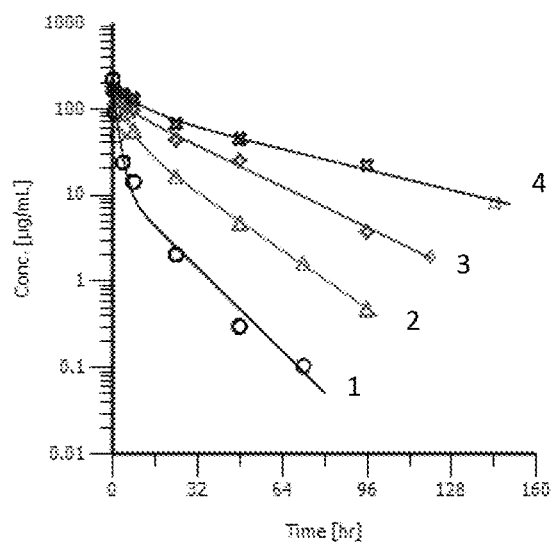
Figures 1C, 1D:
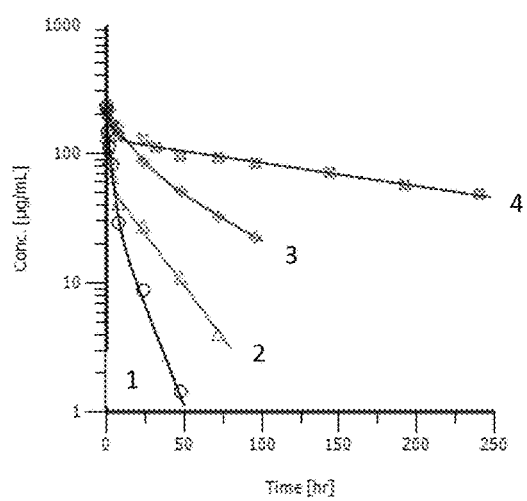

Determination of Pharmacokinetic (PK) Parameter for a PEGylated Anti-hepcidin Lipocalin Mutein in Mice, Rats and Cyno Main pharmacokinetic (PK) parameters for the hNGAL mutein having the sequence of SEQ ID NO: 1 linked to PEG12, PEG20, PEG30 or PEG40 were determined following i.v. single bolus administration in mice, rats and Cynomolgus monkey (*Macacca fascicularis*) at a dose of 10 mg/kg and three animals per sampling time point. Plasma was prepared from blood samples taken at pre-determined time points and the concentrations of the total lipocalin mutein were determined by a sandwich ELISA using an affinity purified hNGAL-specific rabbit antibody preparation (Pieris, PL854) as a capturing step and a biotinylated affinity purified hNGAL-specific rabbit antibody preparation (Pieris, PL1047) for detection of the bound conjugate. Pharmacokinetic calculations were performed by means of the pharmacokinetic software package WinNonlin Professional 5.2 (Pharsight Corporation, USA; 2007). The mean plasma levels (arithmetic mean) versus time profiles for the four test substances are shown in a semi logarithmic plot (FIG. 1a, FIG. 1b and FIG. 1c). A summary of the main pharmacokinetic parameters calculated by two-compartmental analysis for the four test substances in mice, rats and cyno after i.v. administration of 10 mg/kg is presented in the table in FIG. 1d. The results demonstrate that the PK properties of the lipocalin mutein can be adjusted through the choice of PEG and PK parameters such as volume of distribution and clearance from the three species can be used to predict human half-life by allometric scaling.

Example 2

Human PK Parameters

The experimentally determined values for volume of distribution, $V_D$ and clearance, $C_L$ in mice, rat and cyno for each PEGylated version of a lipocalin mutein having the sequence of SEQ ID NO: 1 as determined in the single dose PK studies from Example 1 were used to predict human PK parameters by allometric scaling. The volume of distribution, $V_D$ or clearance, $C_L$ was plotted against body weight of the animals used in the study on a double logarithmic scale and fitted by linear regression. Linear regression was used to extrapolate the values for human volume of distribution, $V_D$ and clearance, $C_L$ of the PEGylated lipocalin muteins. In addition, elimination rate constant and human half-life can be calculated as $k_{el}=V_D$ and $t_{1/2}=\ln 2/k_{el}$. As shown in FIG. 2c, predicted human half-life range from about 5.6, 17, 50 and 298 hours, respectively, for various PEGylated versions of the lipocalin mutein.

Example 3

Determination of Binding Affinity of a PEGylated Anti-hepcidin Lipocalin Mutein in Solution To achieve site-directed PEGylation, the serine at position 87 of the hNGAL mutein having the sequence of SEQ ID NO: 2 was back-mutated to a cysteine that originally occurs in hNGAL wild type by site-directed mutagenesis (Quickchange mutagenesis Kit, Stratagene). The resulted hNGAL mutein having a free cysteine residue at amino acid position 87 (SEQ ID NO: 1) were used for PEGylation with linear (e.g. PEG12, PEG20, PEG30) or branched (PEG40) PEG-maleimide. Prior to the PEGylation reaction, the free cysteine residue was reduced in a 1:1 molar ratio of the lipocalin mutein with TCEP for 3 h at RT. Thereafter, PEGylation was performed by mixing the protein with >2 molar excess of PEG-maleimide reagent for 1.5 h at RT.

The binding affinity of the hNGAL mutein having the sequence of SEQ ID NO: 2 was compared to the binding affinity of the hNGAL mutein having the sequence of SEQ ID NO: 1 linked to PEG12, PEG20, PEG30 or PEG40 in a solution competition electrochemiluminescence (ECL) assay. A defined molar concentration of Hepcidin-25 containing a C-terminal biotin group (25 pM, Hepcidin-25-C-bio) was incubated with different concentrations of the lipocalin muteins for 30 min. at room temperature. The solution was then transferred to an ECL plate coated with the human hepcidin specific monoclonal antibody 12B9 as described herein (and disclosed in WO2008/097461) to measure the remaining concentration of free Hepcidin-25-C-bio in the solution. 12B9-bound Hepcidin-25-C-bio was detected via the Streptavidin sulfotag detection reagent on the Meso-Scale ECL platform and the concentration determined via a Hepcidin-25-C-bio standard curve. The solution binding assay was sufficiently sensitive to distinguish affinities in the lower pM range, as a very low concentration of 25 pM Hepcidin-25 was used. The assay, for example, was able to distinguish the binding affinity of one lipocalin mutein (SEQ ID NO: 2) from the binding affinity of another lipocalin mutein (SEQ ID NO: 3). Furthermore, it allowed a direct comparison of different high affinities of the lipocalin muteins as well as conjugates having PEG chains of different length. The assay was performed several time and average IC50 values and standard deviations are reported in FIG. 3. The results demonstrated that the lipocalin mutein having the sequence of SEQ ID NO: 1 can be conjugated with PEG of different size via a free cysteine without materially affecting the binding affinity of the lipocalin mutein.

Example 4

Figures 5A, 5B:
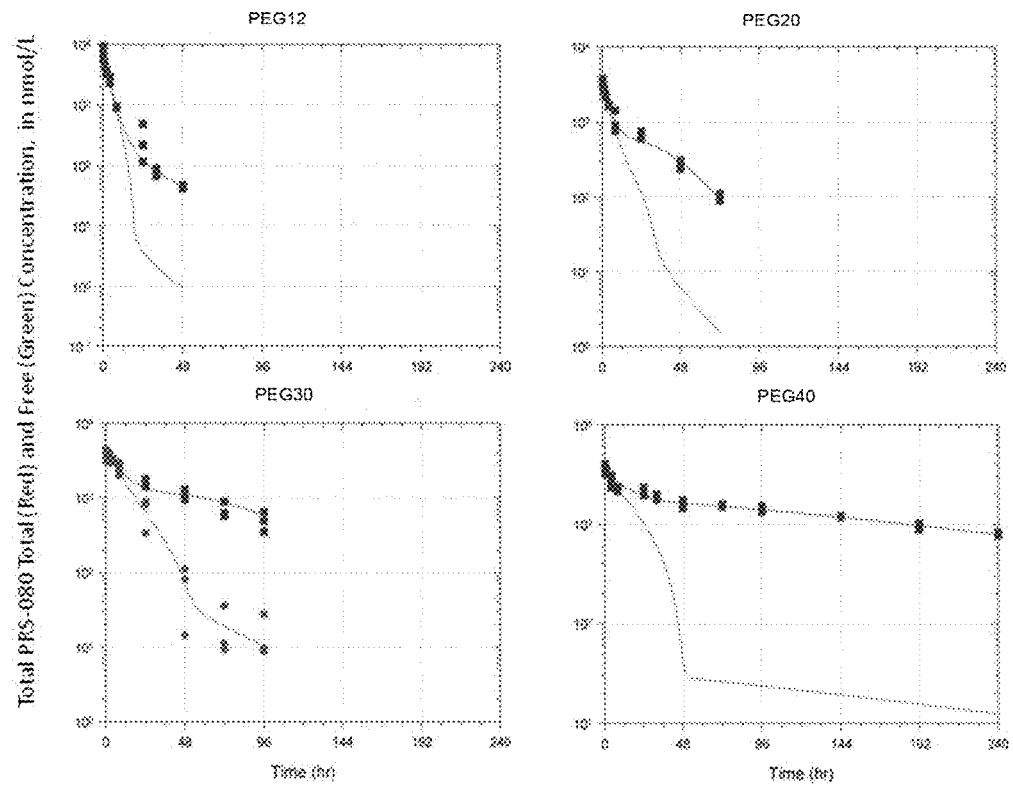
FIGS. 5a-5b show the measured (symbols) and model-predicted (line) concentration-time profiles for total (red) and free (green) concentrations of a lipocalin mutein linked to PEG12, PEG20, PEG30 or PEG40 after a single i.v. dose of 10 mg/kg in Cynomolgus monkeys (n=3). In addition, the respective model derived parameters are show. In particular, measured (symbols) and model-predicted (line) concentration-time profiles for total (red) and free (green) concentrations of a lipocalin mutein linked to PEG12, PEG20, PEG30 or PEG40 after a single i.v. dose of 10 mg/kg in Cynomolgus monkeys (n=3) are shown in FIG. 5a. Pharmacokinetic and pharmacodynamic parameters for mutein PEG conjugates. Kon, Koff, and Kout,h were fixed to values determined prior to this analysis. The respective model derived parameters are shown in FIG. 5b.
Figure 6A:
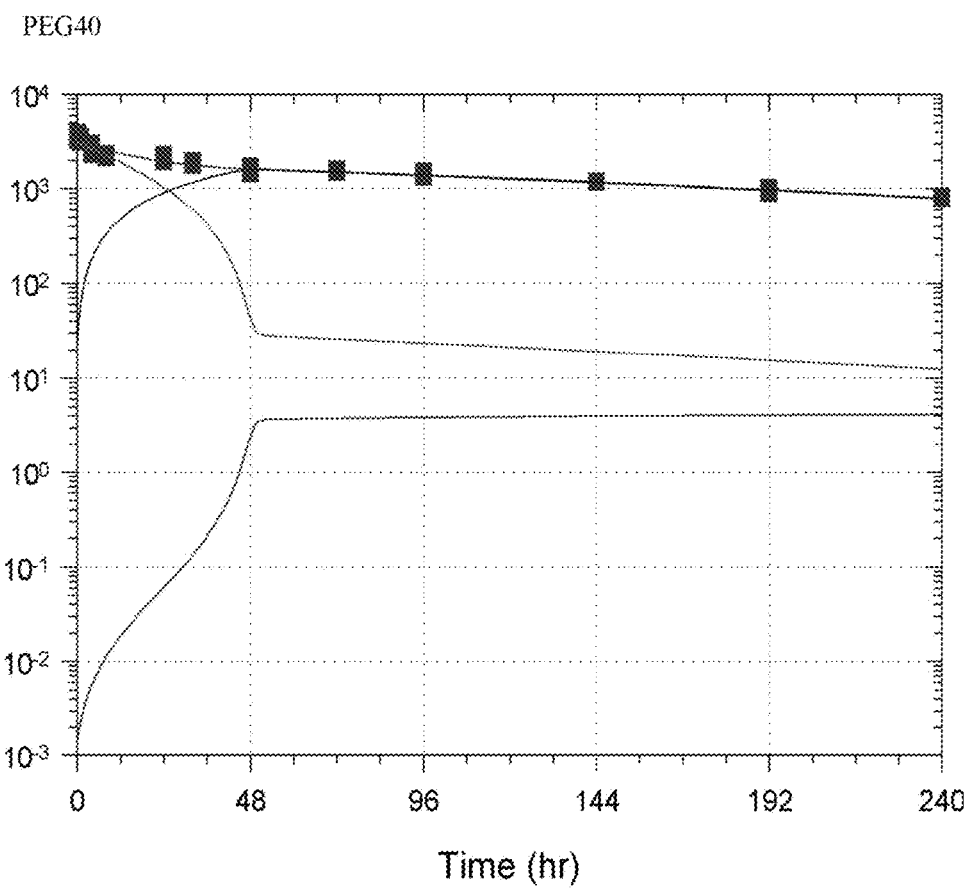
FIGS. 6a-6d show the simulated concentration-time profiles (nMol) of total (bound and unbound) lipocalin mutein (red), hepcidin-mutein complex (blue), free lipocalin mutein (green) and free hepcidin (red) after single administration of 10 mg/kg of a PEGylated lipocalin mutein to Cynomolgus monkeys. The FIGS. 6a-6d also show simulated concentration-time profiles (nMol) of total (bound and unbound) conjugate (red), hepcidin-conjugate complex (blue), free conjugate (green) and free hepcidin (red) after single dose administration of 10 mg/kg of four PEG conjugates of a lipocalin mutein to Cynomolgus monkeys.
Figure 6B:
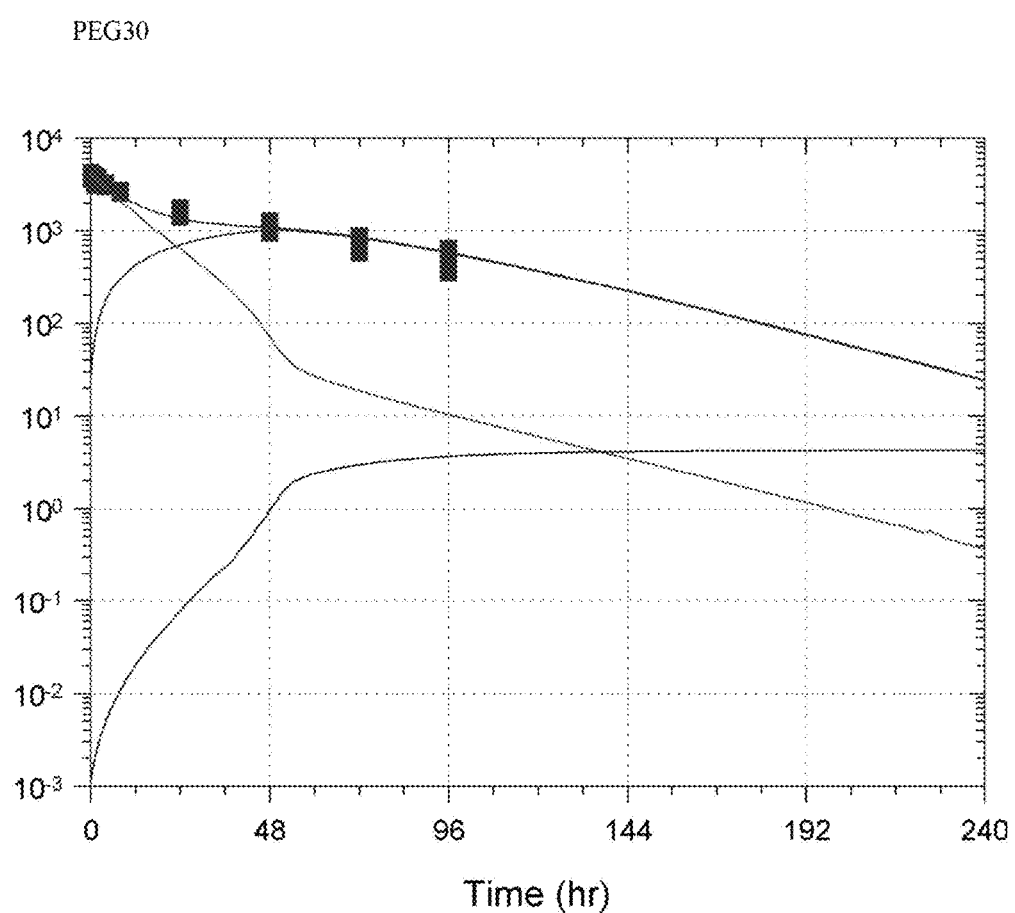
Figure 6C:
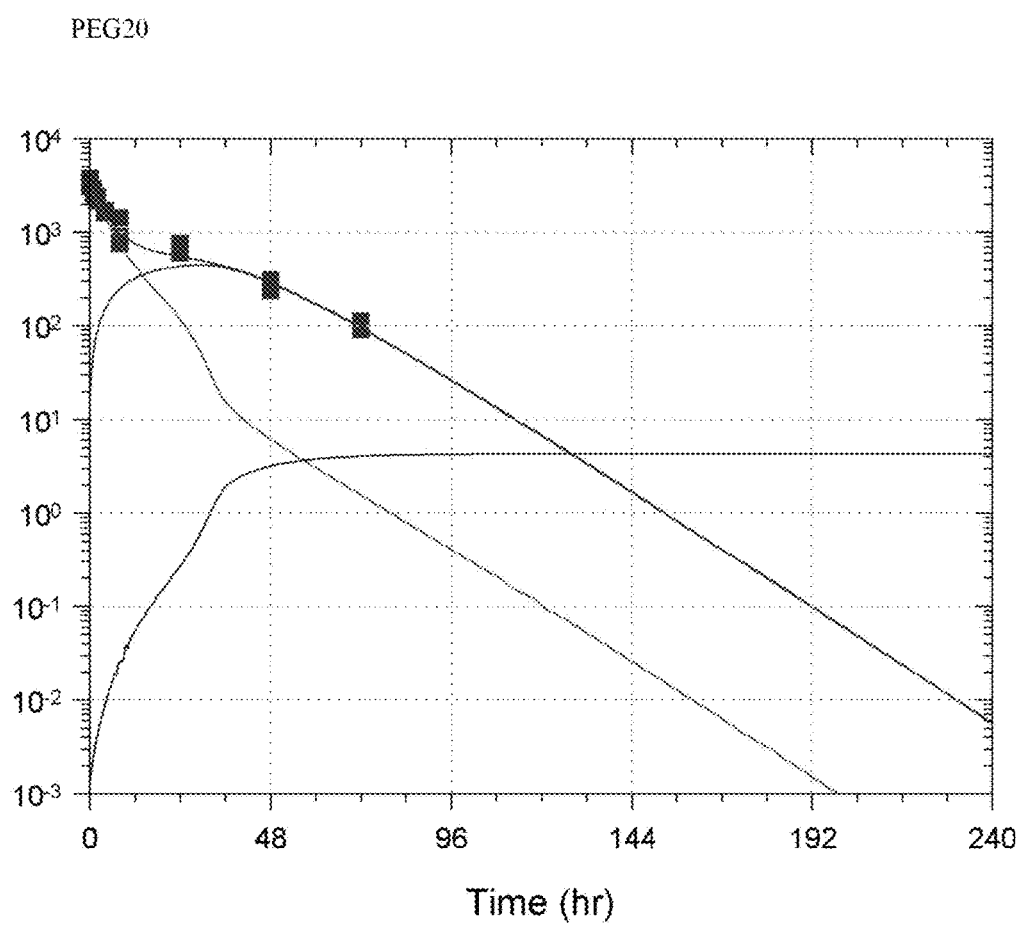
Figure 6D:
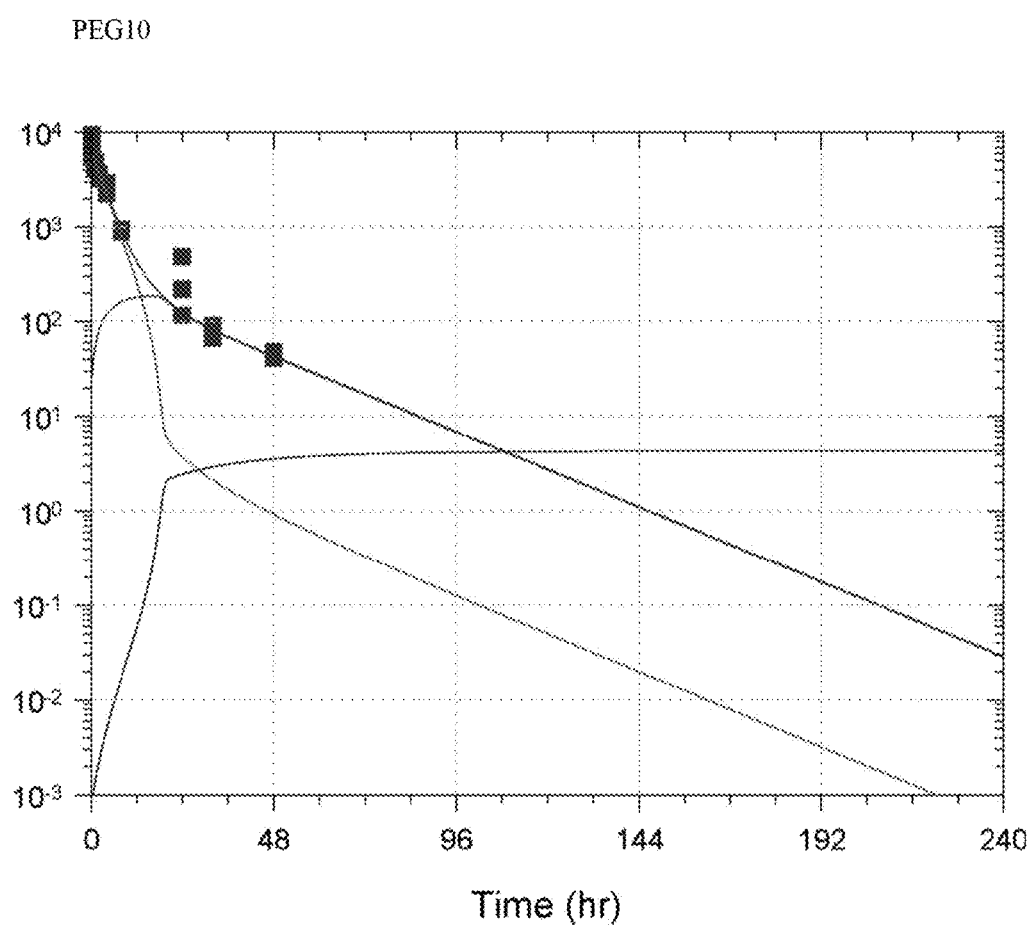

Determination of a Hepcidin-free PEG Conjugate of an Anti-hepcidin Lipocalin Mutein in Cynomolgus Monkeys Plasma concentrations of a hepcidin-free conjugate (lipocalin mutein having the sequence of SEQ ID NO: 1 linked to PEG30) were determined, following i.v. single bolus administration in three Cynomolgus monkeys (*Macacca fascicularis*) at a dose of 10 mg/kg. Plasma was prepared from blood samples taken at pre-determined time points and the concentrations of the hepcidin-free conjugate were determined by a sandwich ELISA using Hepcidin-25-C-bio, immobilized via strepavidin as a capturing step, and a polyclonal rabbit hNGAL-specific antibody preparation (Pieris, PL713) for detection of bound conjugate. In addition, the concentration of total conjugate were determined by a sandwich ELISA using an affinity purified hNGAL-specific rabbit antibody preparation (Pieris, PL854) as a capturing step and a biotinylated affinity purified hNGAL-specific rabbit antibody preparation (Pieris, PL1047) for detection of the bound conjugate. The measured plasma concentrations at different time points for total and hepcidin-free conjugates in individual animals are shown in a semi logarithmic plot (FIG. 5a, left bottom). The comparison of total and free lipocalin-mutein-PEG30 conjugate concentration profiles show that target-binding contributes significantly to the clearance of hepcidin-free conjugate. The data can also be used to predict hepcidin production rates based on the saturation rate of free lipocalin-mutein-PEG30 conjugate and can provide a rational basis for selection of the dose level and dosing regimen for repeat dose studies in preclinical and clinical setting.

Example 5

PK/PD Model

A PK/PD model for the interaction between hepcidin and PEG conjugates having the hNGAL mutein of SEQ ID NO: 1 linked to PEG12, PEG20, PEG30 or PEG40, respectively, was developed based on the model described by Xiao et al (Pharmacokinetics of Anti-hepcidin Monoclonal Antibody Ab 12B9m and Hepcidin in Cynomolgus Monkeys, AAPS J 2010, 12(4):646-57). The model consisted of a two compartment pharmacokinetic model for the conjugates, a turnover model for endogenous hepcidin, and a reversible binding model for the interaction between the conjugates and hepcidin. The model structure is illustrated in FIG. 4. Pharmacodynamic parameters from the publication by Xiao et al. were used for modelling the turnover kinetics of hepcidin. Binding constants for the interaction between the conjugates and Cynomolgus hepcidin 25 as determined by surface plasmon resonance: Kon 3.74 106 M-1s-1, Koff 2.45 10-4 s-1, Kd 0.066 nM were used as additional input on the model. The established PK/PD model was fitted to the experimental total conjugate concentrations in Cynomolgus monkeys using nonlinear regression analysis. After inclusion of an elimination pathway for the conjugate-hepcidin complex using the same first-order elimination rate constant as for free mutein, the model could well describe the observed data as shown in FIG. 5a. By keeping the estimated value for kout,h and the measured hepcidin baseline constant, the developed modelling approach could describe the concentration-time profiles for all four PEG conjugates. The respective model derived parameters are shown in FIG. 5b.

Since there were no data available on the volume of distribution of hepcidin, the model assumed it to be identical to the Vc of the muteins (in analogy to Xiao et al.).

Example 6

PK/PD Simulations

Based on the established PK/PD model and the model derived parameters for each of the four conjugates (having the hNGAL mutein of SEQ ID NO: 1 linked to PEG12, PEG20, PEG30 or PEG40, respectively), simulations were performed to explore the time courses after free hepcidin and hepcidin complex with the assumption that the volume of distribution for both of these moieties is identical to the volume of distribution for free conjugates. concentration-time profiles (nMol) of total (bound and unbound) conjugates (red), hepcidin-conjugate complex (blue), free conjugates (green) and free hepcidin (red) after administration of 10 mg/kg of each conjugate to Cynomolgus monkeys were simulated and shown in FIGS. 5a-5b and FIGS. 6a-6d. The single dose simulations clearly indicate that the free hepcidin concentration is determined by the absolute amount of the conjugates available for binding hepcidin and that the disappearance of free conjugates is largely driven by the hepcidin synthesis rate (kin,h) rather than the elimination rate constant for the conjugates, especially for those conjugates with longer terminal half-life. The comparison of the profiles for the PEG30 and PEG40 conjugates reveals that the reduced clearance and thus longer half-life of the PEG40 conjugate only prolongs the circulation and increases the accumulation of the hepcidin-conjugate complex, but does not prolong the time period for hepcidin suppression, for example, below 1 nM. The model furthermore predicted that a constant suppression of serum hepcidin below a threshold value of 1 nM can be achieved upon repeat dose with both PEG30 and PEG40 conjugates as shown in FIGS. 7a-7b. Nevertheless, repeat administration of the PEG40 conjugate leads to an approximate 5× higher accumulation of conjugate/hepcidin complexes at steady state compared to the PEG30 conjugate.

Example 7

Figure 8:
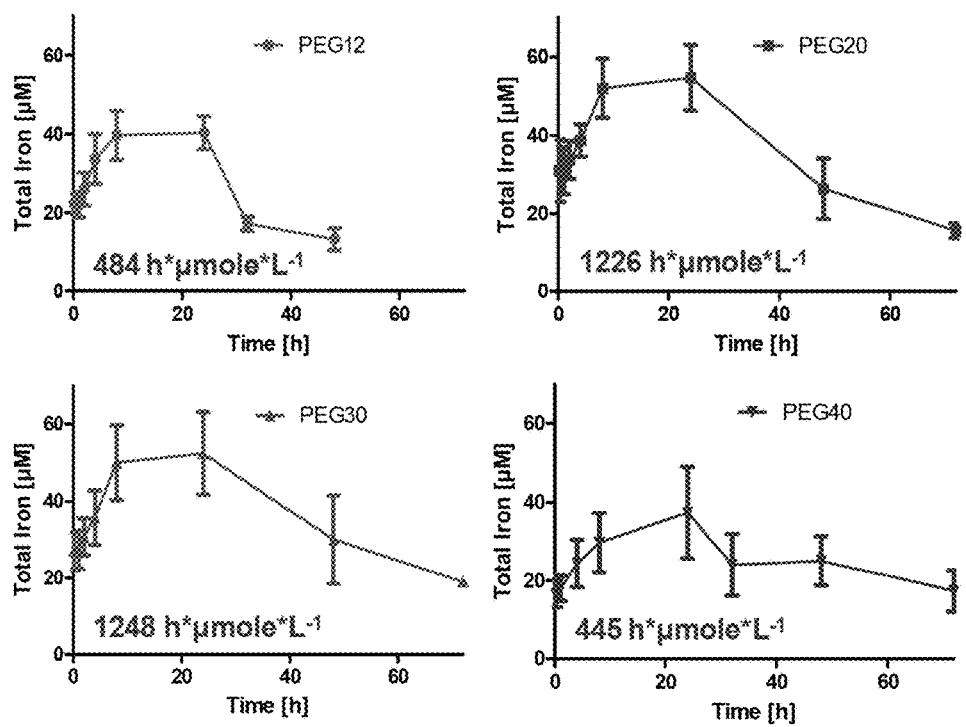
FIG. 8 shows serum iron concentration versus time profiles of a lipocalin mutein linked to PEG12, PEG20, PEG30 or PEG40 after a single i.v. dose of 10 mg/kg in Cynomolgus monkeys (n=3). In particular, the FIG. 8 shows serum iron concentration versus time profiles of four PEG conjugates of a lipocalin mutein after a single i.v. dose of 10 mg/kg in Cynomolgus monkeys (n=3). Values for the serum iron area under the curve are indicated below the respective profiles in h*μmole*L$^{-1}$.

Determination of Serum Iron Concentration in Cynomolgus Monkey after Administration of a Single i.v. Dose of the PEG12, PEG20, PEG30 and PEG40 Conjugates of a Lipocalin Mutein Serum iron concentrations were determined in Cynomolgus monkeys following i.v. single bolus administration at a dose of 10 mg/kg of the PEG12, PEG20, PEG30 or PEG40 conjugates of the lipocalin mutein of SEQ ID NO: 1 (n=3 animals per conjugate). The average serum iron levels from three animals versus time profiles are shown in FIG. 8.

The results demonstrated that a single dose of a PEG conjugate of the hepcidin-specific lipocalin mutein can significantly enhances the serum concentration (bioavailability) of iron in the blood of normal (non-anemic) Cynomolgous monkeys over an extended period of time. The results furthermore suggested that the lipocalin mutein effectively antagonizes the functional activity of hepcidin in vivo by preventing hepcidin-induced ferroportin internalization and degradation and thereby enhances the mobilization (cellular export) of iron from iron tissue stores. Similar responses were seen with PEG20, PEG30 and PEG40 conjugates while PEG12 conjugate resulted in lower peak serum iron levels and shorter duration of elevated serum levels above baseline.

Example 8

Figure 9:
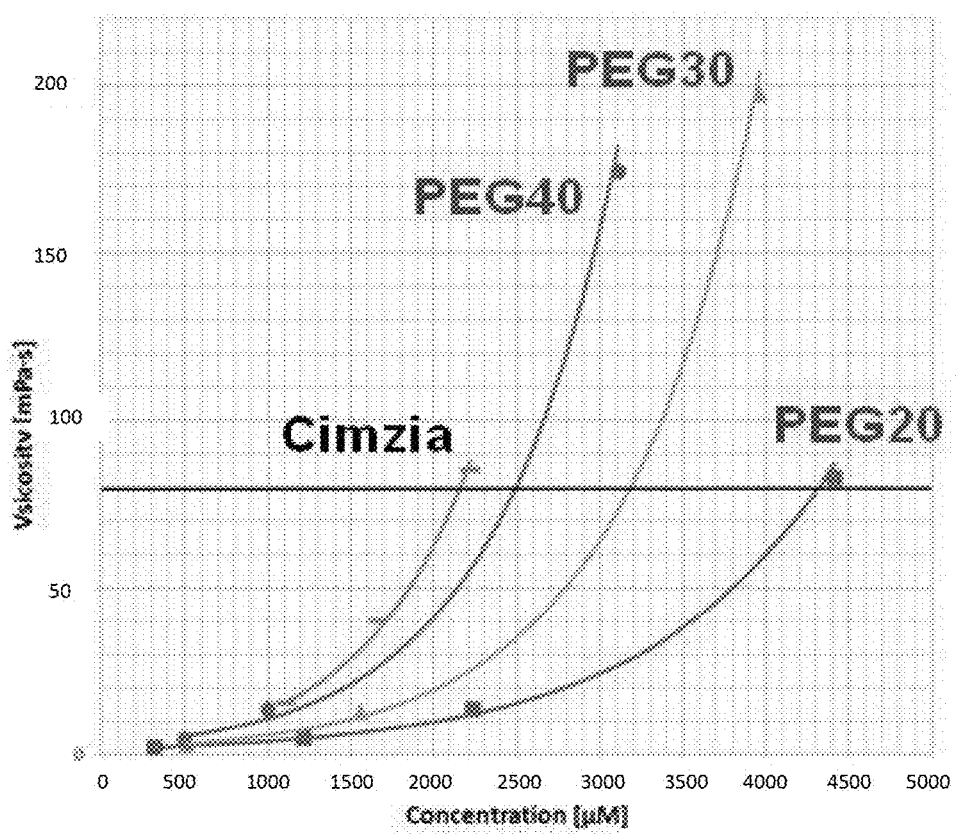
FIG. 9 shows the viscosity of three PEG conjugates of a lipocalin mutein at different molar concentrations.
Figure 10A:
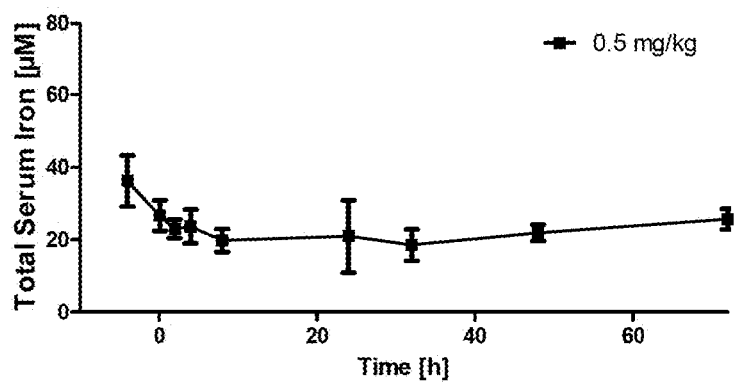
FIGS. 10a-10d show the iron response of Cynomolgus monkeys (n=3) dependent on the i.v. dose of a lipocalin mutein linked to PEG30. In particular, the FIGS. 10a-10d show serum iron concentration versus time profiles of a lipocalin mutein linked to PEG30 after a single i.v. dose of 0.5-10 mg/kg or the parental wild type lipocalin linked to PEG40 at 10 mg/kg in Cynomolgus monkeys (n=3). Values for the serum iron area under the curve (if any) are indicated below the respective profiles in h*μmole*L$^{-1}$.
Figure 10B:
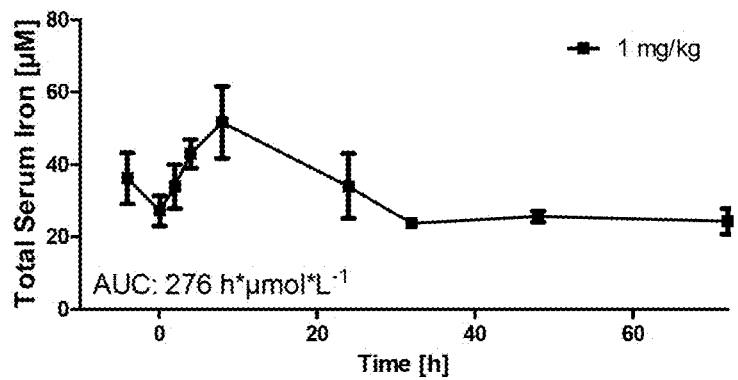
Figure 10C:
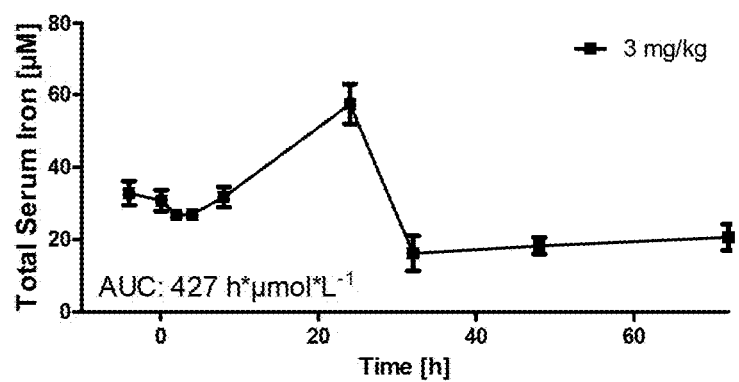
Figure 10D:
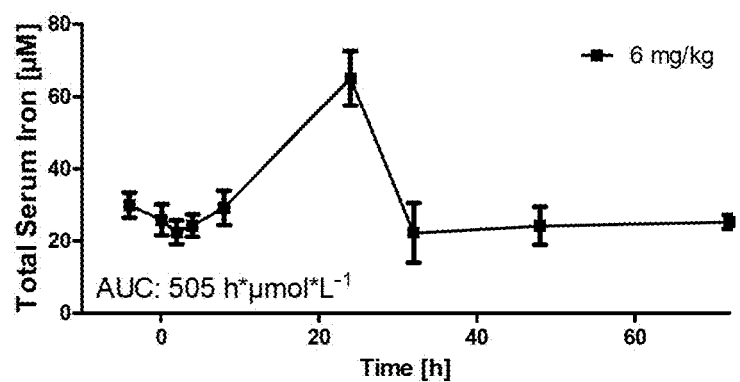
Figure 10E:
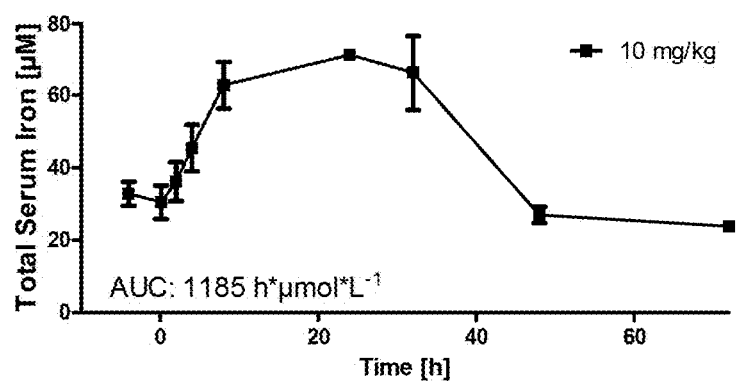
Figure 10F:
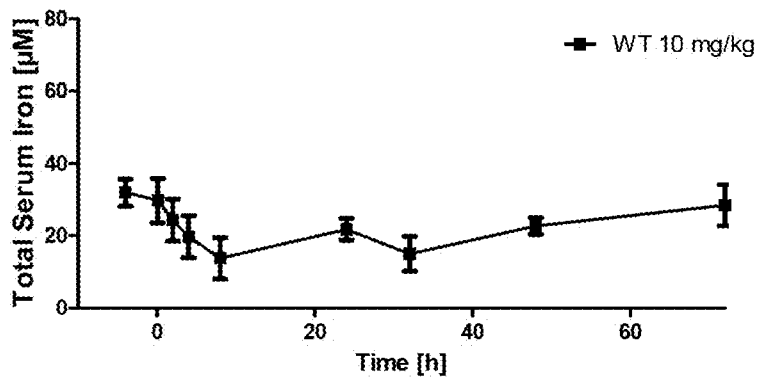
Figure 11A:
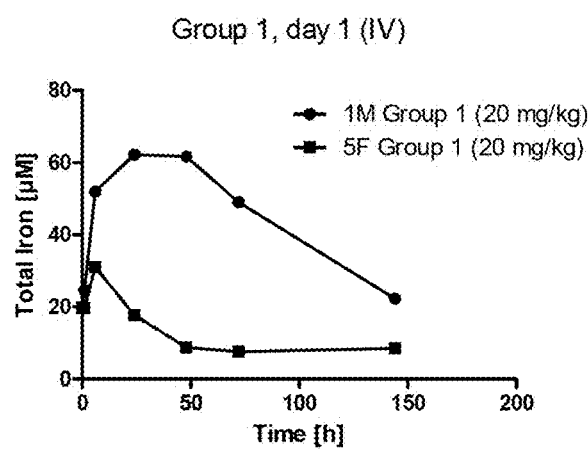
FIGS. 11a-11e show the iron response in individual Cynomolgus monkeys when dosed once i.v. or subcutaneous (s.c.) with large amounts of a lipocalin mutein linked to PEG30. In particular, the FIGS. 11a-11e show serum iron concentration versus time profiles of a lipocalin mutein linked to PEG30 after a single i.v. dose of 20/40/80/150 mg/kg and single s.c. dose of 20 mg/kg in Cynomolgus monkeys.
Figure 11B:
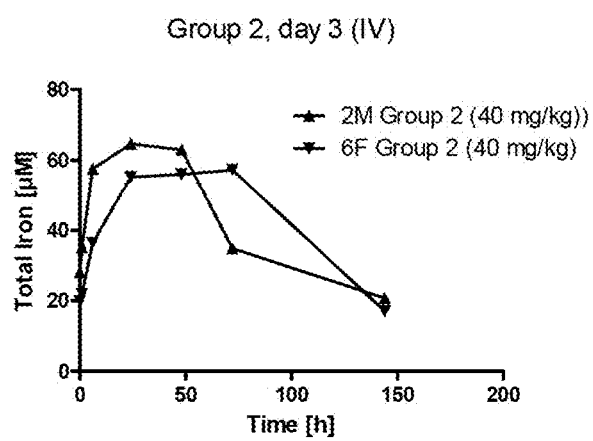
Figure 11C:
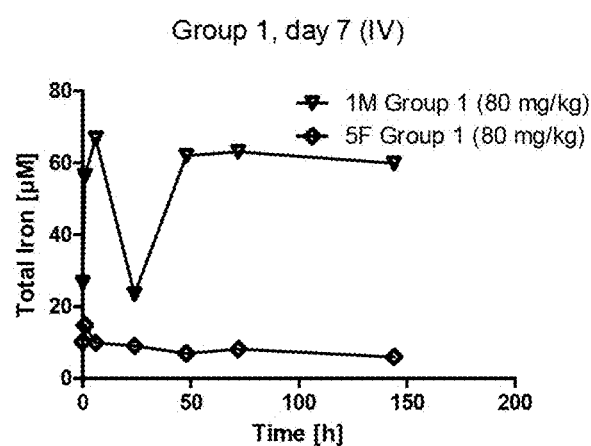
Figure 11D:
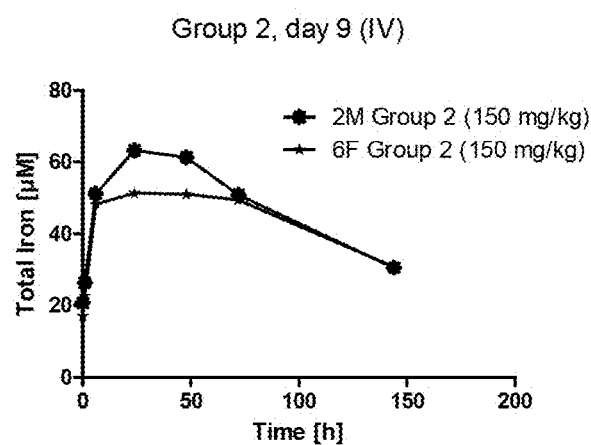
Figure 11E:
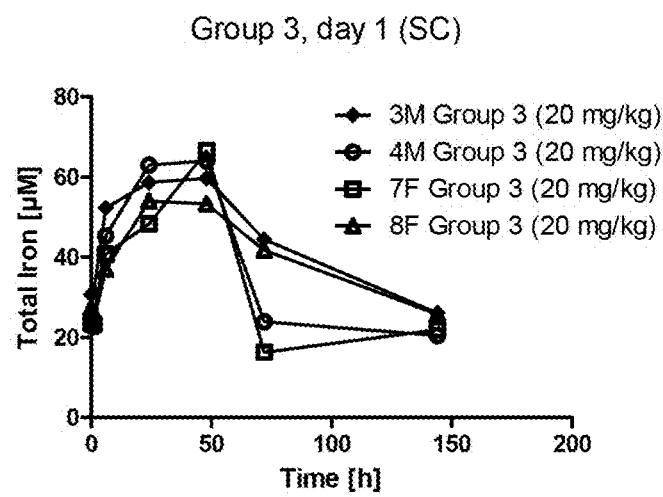

Determination of Viscosity of the PEG20, PEG30 and PEG40 Conjugates of a Lipocalin Mutein Versus the Viscosity of Cimzia at Different Molar Concentrations As showed in FIG. 9, the conjugates were concentrated in a step-wise manner with spin columns without optimization of the formulation (pH, buffer systems or excipients), while Cimzia (certolizumab pegol, UCB) was already formulated for clinical use at 200 mg/ml was diluted in phosphate buffered saline. The absence of protein aggregation (<2% dimer or aggregates) was confirmed by HP-SEC of non-diluted samples. The viscosity was measured with the Rheo-Sense m-VROC viscometer (RheoSense) of a 100 µl sample and a 10-200 µl/min flow rate. Average viscosity values were calculated from 2-3 analytical runs. 80 mPa·s was defined as viscosity/syringeability threshold that would allow the use of a 25G ½ inch thin wall needle for s.c. injection based on the observed viscosity of Cimzia, a 40 kDa PEGylated Fab fragment, formulated as 200 mg/ml solution for s.c. injection with a 25G ½ inch thin wall needle. The results demonstrate that PEGylated forms of the hepcidin-specific mutein having the sequence of SEQ ID NO: 1 can be easily concentrated above 150 mg/ml. The viscosity of PEG conjugates of the lipocalin mutein increases with the PEG size.

Therefore, shorter PEG moieties would support formulations with higher concentrations that are still syringeable, for example, for subcutaneous injection.

Example 9

Determination of the Iron Response of Cynomolgus Monkeys (n=3) Dependent on the i.v. Dose of a Lipocalin Mutein Linked to PEG30

Serum iron concentrations were determined in Cynomolgus monkeys following i.v. single bolus administration at a dose of 0.5/1/3/6/10 mg/kg of the hepcidin-specific lipocalin mutein having the sequence of SEQ ID NO: 1 linked to PEG30 (n=3 animals per dose level) and following i.v. single bolus administration at a dose of 10 mg/kg of the hNGAL (SEQ ID NO: 4) linked to PEG40. The average serum iron levels from three animals versus time profiles are shown in FIGS. 10a-10f. The results demonstrated a dose dependent pharmacological activity in regard to iron mobilization and indicated that 1-3 mg/kg constitute a minimal biological effect level.

Example 10

Determination of the Iron Response in Individual Cynomolgus Monkeys when Dosed Once i.v. or s.c. at High Dose Levels of a Lipocalin Mutein Linked to PEG30

Serum iron concentrations were determined in Cynomolgus monkeys following a singe i.v. infusion over 30 min. at a dose of 20/40/80/150 mg/kg and following s.c. single bolus administration at a dose of 20 mg/kg of the hepcidin-specific mutein having the sequence of SEQ ID NO: 1 linked to PEG30 in individual animals. A standard formulation of 20 mg/ml was used for both routes of administration (i.v. and s.c.). A staggered approach was used where group 1 animals were dosed with 20 mg/kg followed by a wash out period of 6 days prior to dosing with 80 mg/kg whereas group 2 animals were dosed with 40 mg/kg followed by a wash out period of 6 days prior to dosing with 150 mg/kg. The iron levels from individual animals versus time profiles are shown in FIGS. 11a-11e. The results, as shown in FIGS. 10a-10f and FIGS. 11a-11e, indicated that the hyperferremia induced by hepcidin inhibition through the lipocalin mutein was capped at a maximum serum iron of 65 µM ($C_{max}$). Serum iron $C_{max}$ was reached already at dose levels of 3-6 mg/kg and did not increase at higher doses of 10-150 mg/kg. Nevertheless, the iron response even at high doses is transient and reversible. Furthermore, the results in FIGS. 11a-11e showed that the onset, magnitude and duration of the iron response is comparable between s.c. and i.v. administration at least at a saturating dose level of 20 mg/kg.

Example 11

Determination of the Iron Response in Individual Cynomolgus Monkeys when Dosed Repeatedly i.v. or s.c. with Large Amounts of a Lipocalin Mutein Linked to PEG30

Figure 12:
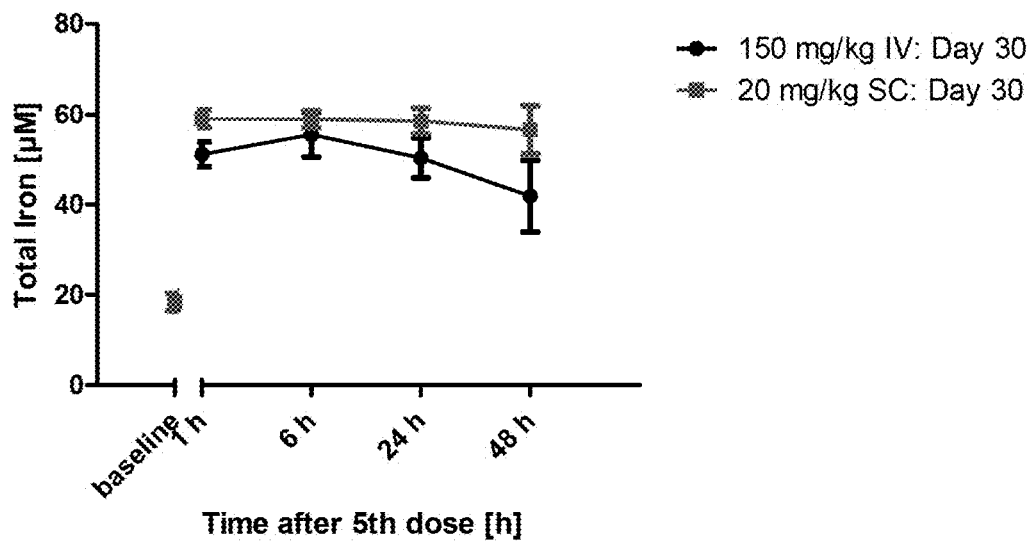
FIG. 12 shows the iron response in individual Cynomolgus monkeys when dosed repeatedly i.v. or s.c. with large amounts of a lipocalin mutein linked to PEG30. In particular, the FIG. 12 shows serum iron concentration versus time profiles (mean+/−SEM, n=3, one non-responder per group excluded) of a lipocalin mutein linked to PEG30 after repeat (5×Q2D) i.v. or s.c. at 150 mg/kg or 20 mg/kg respectively.

Total serum iron concentrations were determined in Cynomolgus monkeys following repeat i.v. infusion (30 min.) and s.c. bolus administration at a dose of 150 mg/kg and 20 mg/kg, respectively, of the hepcidin-specific mutein having the sequence of SEQ ID NO: 1 linked to PEG30 in individual animals. A standard formulation of 20 mg/ml was used for both routes of administration (i.v. and s.c.). Four animals per group were dosed 5 times every second day after a washout period of at least 14 days following the single i.v. and s.c. administration as described in Example 10. Total plasma iron profiles (mean+/−SD, n=3, one non-responder per group excluded) after administration of the $5^{th}$ dose are, as shown in FIG. 12, up to the time of necropsy at 48 hours. The results showed that a similar iron response could be observed after repeat dose compared to a first dose as shown in FIGS. 11a-11e. Again, total serum iron $C_{max}$ was capped at 65 µM after repeat administration. Furthermore, no tolerance or counter-regulatory mechanisms appeared to reduce the pharmacological effect of the lipocalin mutein mediated hepcidin inhibition and consequential plasma hyperferremia.

Example 12

Measurement of Specificity of a Lipocalin Mutein Using Biacore

The affinity and binding specificity of a lipocalin mutein was determined in a kinetic assay using surface plasmon resonance. The hepcidin-specific lipocalin mutein having the sequence of SEQ ID NO: 1 and the hNGAL lipocalin having the sequence of SEQ ID NO: 4 were immobilized to a level of 750-1100 resonance units (RU) on a CM5 sensor chip (GE Healthcare, BR-1005-30) using an amine coupling kit (GE Healthcare, BR-1000-50). Residual activated groups were saturated with ethanolamine. The reference channels were treated with EDC/NHS following ethanolamine (blank immobilization). Dilutions of Hepcidin-25 (Peptalova), Fe-enterobactin (Genaxxon Bioscience, S4035.0001), β-defensin (Sigma Aldrich, D9565), $VEGF_{8-109}$ (Pieris, truncated VEGF) and HSA (Sigma Life sciences, A1653) in HBS-EP+ buffer (GE Healthcare, BR-1006-69) were applied to the prepared chip surfaces. The following parameters were used for the binding assay: contact time 60 s, dissociation time 600 s, flow rate 30 µL/min. All measurements were performed on a Biacore T200 instrument (GE Healthcare) at 25° C. Regeneration of the immobilized lipocalin mutein surface was achieved with subsequent injections of 2 M Guanidinium-HCl (600 s) and 10 mM glycine-HCl pH 2.0 (210 s) followed by an extra wash with running buffer and a stabilization period of 210 s. Prior to the protein measurements three startup cycles were performed for conditioning purposes. Data were evaluated with Biacore T200 Evaluation software (V 1.0). Double referencing was used. The 1:1 Binding model was used to fit the raw data. No binding to the reference channel was detected for all of the targets. FIG. 13a shows that the lipocalin mutein bound Hepcidin-25 with picomolar affinity while it did not exhibit any measurable affinity towards the other analytes that were tested. As shown in FIG. 13b, the affinity of the lipocalin mutein for Cynomolgous hepcidin 25 was identical including identical $K_{on}$ and $K_{off}$ rates compared to Hepcidin-25 when tested in the same assay format. The bacterial siderophor Fe-enterobactin was selected for this analysis as it constitutes one of the natural ligands of the lipocalin that the lipocalin mutein was derived from. The mammalian antimicrobial 36 amino acid peptide β-defensin was selected for this analysis as it shows several structural similarities to hepcidin, namely 3 disulfide bonds, anti-parallel β sheets and a β-turn even though the sequence identity is very low with 24%. HSA and VEGF were used as example of non-related proteins. The hNGAL lipocalin, immobilized in an identical fashion on a CM5 chip compared to the lipocalin mutein was used as positive control for the Fe-enterobactin analyte. As described in the literature, the hNGAL lipocalin bound Fe-enterobactin with subnanomolar affinity, whereas none of the other analytes including hepcidin were bound.

The invention has industrial applications in connection with treatment of diseases and/or conditions associated with decreased levels of iron. The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. All patents, patent applications, text books and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also form part of the invention.

This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A pharmaceutical composition comprising a lipocalin mutein or fragment thereof having binding affinity to hepcidin, wherein the lipocalin mutein has the same amino acids as the mutein set forth in SEQ ID NO: 1 at two or more positions corresponding to positions 36, 40, 41, 49, 52, 68, 70, 72, 73, 77, 79, 81, 96, 100, 103, 106, 125, 127, 132, and 134 of the linear polypeptide sequence of mature hNGAL, and wherein the lipocalin mutein or fragment is capable of increasing the bioavailability of iron in a subject in need thereof.

2. The pharmaceutical composition of claim 1, wherein said composition is adapted for administration via a parenteral or non-parenteral route.

3. The pharmaceutical composition of claim 1, wherein said composition is adapted for administration via an enteral route.

4. The pharmaceutical composition of claim 1, wherein the lipocalin mutein or fragment thereof is capable of inhibiting binding of hepcidin to a hepcidin specific monoclonal antibody having the variable light chain region shown in SEQ ID No: 6 and the variable heavy chain region shown in SEQ ID No: 7.

5. The pharmaceutical composition of claim 1, wherein the lipocalin mutein or fragment thereof competes for binding to hepcidin with a hepcidin specific monoclonal antibody having the variable light chain region shown in SEQ ID No: 6 and the variable heavy chain region shown in SEQ ID No: 7.

6. The pharmaceutical composition of claim 1, wherein the lipocalin mutein or fragment thereof has the same amino acids as the mutein set forth in SEQ ID NO: 1 at the positions corresponding to positions 36, 40, 41, 49, 52, 68, 70, 72, 73, 77, 79, 81, 96, 100, 103, 106, 125, 127, 132, and 134 of the linear polypeptide sequence of mature hNGAL.

7. The pharmaceutical composition of claim 1, wherein the lipocalin mutein or fragment thereof has at least 75% sequence identity to SEQ ID NO: 1.

8. The pharmaceutical composition of claim 1, wherein the lipocalin mutein or fragment thereof has at least 90% sequence identity to SEQ ID NO: 1.

9. The pharmaceutical composition of claim 1, wherein the lipocalin mutein or fragment thereof has at least 95% sequence identity to SEQ ID NO: 1.

10. The pharmaceutical composition of claim 1, wherein the lipocalin mutein or fragment thereof does not bind to Fe-enterobactin.

11. The pharmaceutical composition of claim 1, wherein the lipocalin mutein or fragment thereof is conjugated to a compound that extends the serum half-life of the lipocalin mutein or fragment thereof.

12. The pharmaceutical composition of claim 11, wherein the compound that extends the serum half-life is selected from the group consisting of a polyalkylene glycol molecule, a hydroxyethyl starch, a protein domain, a Fc part of an immunoglobulin, a CH3 domain of an immunoglobulin, a CH4 domain of an immunoglobulin, an albumin-binding peptide, and an albumin-binding protein.

13. The pharmaceutical composition of claim 12, wherein the lipocalin mutein or fragment thereof is conjugated to a polyalkylene glycol.

14. The pharmaceutical composition of claim 13, wherein the polyalkylene glycol is polyethylene (PEG) or an activated derivative thereof.

15. The pharmaceutical composition of claim 14, wherein the polyethylene (PEG) is 30 kilo Daltons in molecular weight.

16. The pharmaceutical composition of claim 15, wherein the lipocalin mutein or fragment thereof is conjugated to or forms a fusion protein with a moiety selected from the group consisting of an Fc part of an immunoglobulin, a CH3 domain of an immunoglobulin, a CH4 domain of an immunoglobulin, an albumin-binding peptide, and an albumin-binding protein.

17. The pharmaceutical composition of claim 1, wherein the lipocalin fragment lacks at least one of the N-terminal and/or C-terminal amino acids compared to the linear polypeptide sequence of mature hNGAL.

18. The pharmaceutical composition of claim 1, wherein the lipocalin fragment lacks at least ten consecutive of the N-terminal and/or C-terminal amino acids compared to the linear polypeptide sequence of mature hNGAL.

19. The pharmaceutical composition of claim 1, wherein the serum half-life of the lipocalin mutein or fragment thereof is at least 1 day.

20. The pharmaceutical composition of claim 1, wherein the serum half-life of the lipocalin mutein or fragment thereof is at least 2 days.

* * * * *

```
                        SEQUENCE LISTING

<160> NUMBER OF SEQ ID NOS: 7

<210> SEQ ID NO 1
<211> LENGTH: 178
<212> TYPE: PRT
<213> ORGANISM: Artificial
<220> FEATURE:
<223> OTHER INFORMATION: Mutein of hNGAL

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Glu Val Leu Arg Glu Asp Lys Asp Pro
            35                  40                  45

Met Lys Met Trp Ala Thr Ile Tyr Glu Leu Lys Glu Asp Lys Ser Tyr
        50                  55                  60

Asn Val Thr Ile Val Met Pro Leu Ala Glu Lys Cys Glu Tyr Leu Phe
65                  70                  75                  80

Gln Thr Phe Val Pro Gly Cys Gln Pro Gly Glu Phe Thr Leu Gly Gly
                85                  90                  95

Ile Lys Ser Gly Pro Gly Arg Thr Ser Gly Leu Val Arg Val Val Ser
            100                 105                 110

Thr Asn Tyr Asn Gln His Ala Met Val Phe Phe Lys Val Val Trp Gln
        115                 120                 125

Asn Arg Glu Val Phe Trp Val Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial
<220> FEATURE:
<223> OTHER INFORMATION: Mutein of hNGAL

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Glu Val Leu Arg Glu Asp Lys Asp Pro
            35                  40                  45

Met Lys Met Trp Ala Thr Ile Tyr Glu Leu Lys Glu Asp Lys Ser Tyr
        50                  55                  60

Asn Val Thr Ile Val Met Pro Leu Ala Glu Lys Cys Glu Tyr Leu Phe
65                  70                  75                  80
```

Gln Thr Phe Val Pro Gly Ser Gln Pro Gly Glu Phe Thr Leu Gly Gly
                85                  90                  95

Ile Lys Ser Gly Pro Gly Arg Thr Ser Gly Leu Val Arg Val Val Ser
                100                 105                 110

Thr Asn Tyr Asn Gln His Ala Met Val Phe Phe Lys Val Val Trp Gln
            115                 120                 125

Asn Arg Glu Val Phe Trp Val Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial
<220> FEATURE:
<223> OTHER INFORMATION: Mutein of hNGAL

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Glu Val Leu Arg Glu Asp Lys Asp Pro
            35                  40                  45

Met Lys Met Trp Ala Thr Ile Tyr Glu Leu Glu Glu Asp Lys Ser Tyr
        50                  55                  60

Asn Val Thr Ile Val Met Phe Leu Ala Lys Lys Cys Glu Tyr Leu Phe
65                  70                  75                  80

Gln Thr Phe Val Pro Gly Ser Gln Pro Gly Glu Phe Thr Leu Gly Asp
                85                  90                  95

Ile Lys Ser Ser Pro Gly Arg Thr Ser Gly Leu Val Arg Val Val Ser
                100                 105                 110

Thr Asn Tyr Asn Gln His Ala Met Val Phe Phe Lys Thr Val Trp Gln
            115                 120                 125

Asn Arg Glu Val Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial
<220> FEATURE:
<223> OTHER INFORMATION: wild type hNGAL

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 25
<212> TYPE: PRT
<213> ORGANISM: human
<220> FEATURE:
<223> OTHER INFORMATION: Hepcidin-25

<400> SEQUENCE: 5

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 6
<211> LENGTH: 107
<212> TYPE: PRT
<213> ORGANISM: Artificial
<220> FEATURE:
<223> OTHER INFORMATION: variable light chain region of 12B9 antibody
      from WO 2008/097481

<400> SEQUENCE: 6

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Glu Arg Tyr Ala
            20                  25                  30

Cys Trp Tyr Gln Gln Arg Pro Gly Gln Ser Pro Val Leu Val Ile Tyr
        35                  40                  45

Gln Asp Ile Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

-continued

```
Asp Glu Ala Asp Tyr Phe Cys Gln Ala Trp Tyr Ser Ser Thr Asn Val
                85                  90                  95

Leu Phe Gly Gly Gly Thr Lys Leu Thr Val Leu
            100                 105

<210> SEQ ID NO 7
<211> LENGTH: 121
<212> TYPE: PRT
<213> ORGANISM: Artificial
<220> FEATURE:
<223> OTHER INFORMATION: variable heavy chain region of 12B9 antibody
      from WO 2008/097481

<400> SEQUENCE: 7

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Ala Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Glu Gly Ile Ala Pro Asp Ala Phe Asp Ile Trp Gly
            100                 105                 110

Gln Gly Thr Met Val Thr Val Ser Ser
            115                 120
```